(12) United States Patent
Hudyma et al.

(10) Patent No.: US 7,022,667 B2
(45) Date of Patent: Apr. 4, 2006

(54) O-DERIVATIZED NOCATHIACIN DERIVATIVES

(75) Inventors: Thomas W. Hudyma, Durham, CT (US); Xiaofan Zheng, Cheshire, CT (US); B. Narasimhulu Naidu, Durham, CT (US); Margaret E. Sorenson, Meriden, CT (US); Alicia Regueiro-Ren, Middletown, CT (US); Timothy P. Connolly, Middletown, CT (US); John D. Matiskella, Wallingford, CT (US); Oak K. Kim, Cambridge, MA (US); Yunhui Zhang, Glastonbury, CT (US); Dane M. Springer, North Haven, CT (US); Jason Goodrich, Meriden, CT (US); Yasutsugu Ueda, Clinton, CT (US); Joanne J. Bronson, Durham, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 348 days.

(21) Appl. No.: 10/189,710

(22) Filed: Jul. 3, 2002

(65) Prior Publication Data

US 2004/0018963 A1    Jan. 29, 2004

(51) Int. Cl.
*A61K 38/16* (2006.01)
(52) U.S. Cl. .................. 514/8; 514/9; 530/317
(58) Field of Classification Search .............. 514/8, 514/9; 530/317
See application file for complete search history.

(56) References Cited

U.S. PATENT DOCUMENTS

| 6,218,398 B1 | 4/2001 | Leet et al. | |
| 6,287,827 B1 | 9/2001 | Li et al. | |
| 2002/0055465 A1 | 5/2002 | Li et al. | |
| 2002/0065219 A1* | 5/2002 | Naidu et al. ............... | 514/9 |

FOREIGN PATENT DOCUMENTS

| WO | WO 00/03722 | 1/2000 |
| WO | WO 00/14100 | 3/2000 |
| WO | WO 02/13834 | 2/2002 |
| WO | WO 02/14354 | 2/2002 |

* cited by examiner

*Primary Examiner*—Bruce R. Campell
*Assistant Examiner*—Roy Teller
(74) *Attorney, Agent, or Firm*—James Epperson; Samuel J. DuBoff

(57) ABSTRACT

The present invention provides compounds of formula I

I

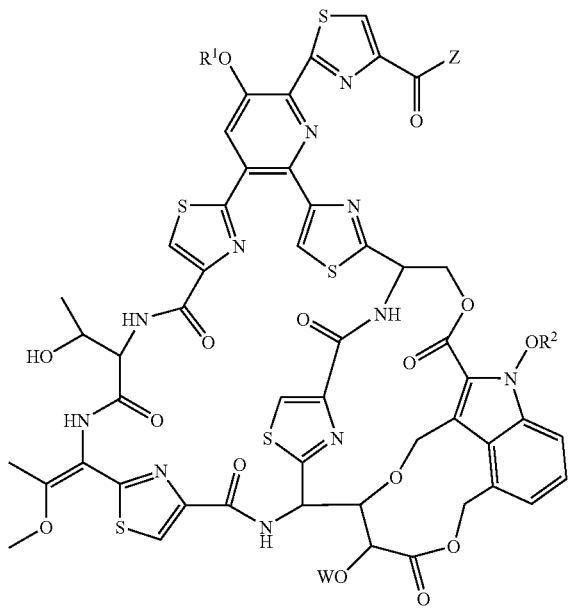

having potent antibiotic activity, including activity towards Gram-positive bacteria and mycobacteria.

9 Claims, No Drawings

O-DERIVATIZED NOCATHIACIN DERIVATIVES

BACKGROUND OF THE INVENTION

Multidrug-resistant strains of many clinically important pathogenic bacteria, including methicillin-resistant *Staphylococcus aureus* (MRSA), *Streptococcus pneumoniae, Mycobacterium tuberculosis*, and *Enterococci* strains are becoming a worldwide health problem. There is an urgent need to discover new agents to treat patients infected with multidrug-resistant bacteria. Many thiazolyl peptide antibiotics possess potent antimicrobial activity against Gram-positive bacteria, including multidrug-resistant strains. Novel nocathiacin derivatives and related thiazolyl peptide derivatives, having inhibitory activity at the nanomolar level against Gram-positive bacteria, have been discovered. The nocathiacin derivatives and related thiazolyl peptide derivatives described herein exhibit potent antimicrobial activity against Gram-positive bacteria in vitro, and exhibit in vivo efficacy in a systemic *Staph. aureus* infection model in animals.

The novel nocathiacin derivatives of this invention are derived from the thiazolyl peptide antibiotic, nocathiacin I or II described by J. E. Leet et al in U.S. Pat. No. 6,218,398, issued Apr. 17, 2001, (corresponding to PCT Appl. WO 00/03722, published Jan. 27, 2000), and nocathiacin IV described by W. Li et al in PCT Appl. WO 02/13834 (published Feb. 21, 2002).

Nocathiacin I has the structure:

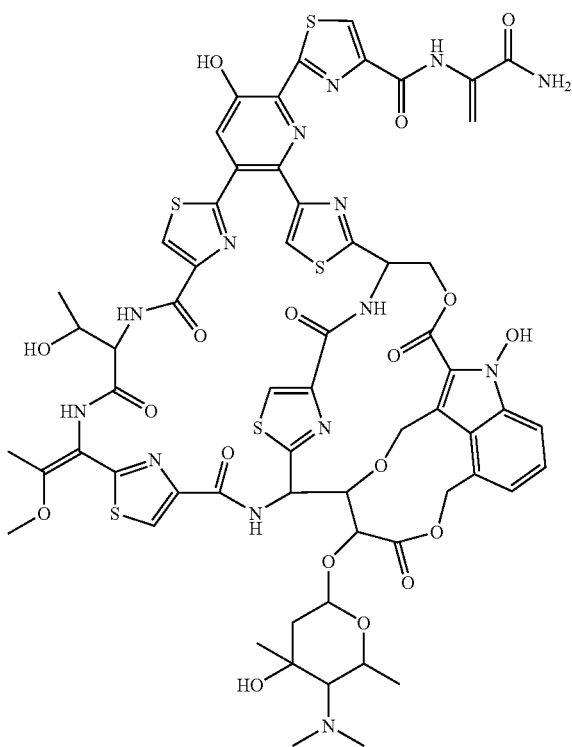

Nocathiacin II is identical in structure to Nocathiacin I, except $OR^2$ is H, rather than OH as in Nocathiacin I.

Other nocathiacin derivatives are described in U.S. Pat. No. 6,287,827 granted Sep. 11, 2001; PCT WO 00/14100 published Mar. 16, 2000; and PCT WO 02/14354 published Feb. 21, 2002.

Neither the novel nocathiacin derivatives described here nor their use in treating infectious diseases is known or suggested by prior art.

SUMMARY OF THE INVENTION

The present invention comprises compounds of Formula I, which is defined below, including pharmaceutically acceptable salts thereof. These compounds possess potent antibiotic activity, including activity towards Gram-positive bacteria and mycobacteria.

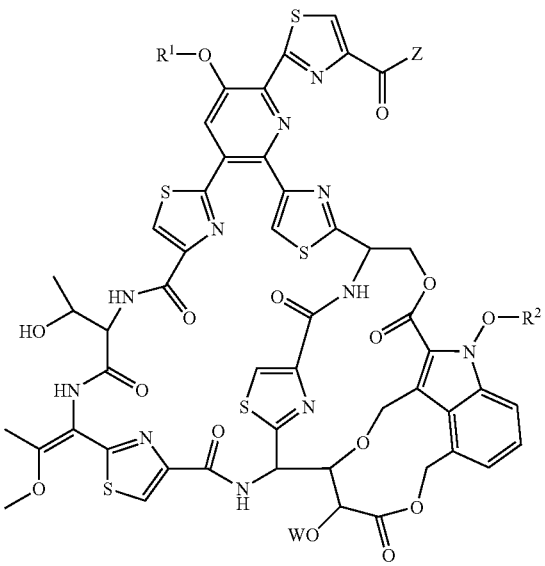

wherein:

W is

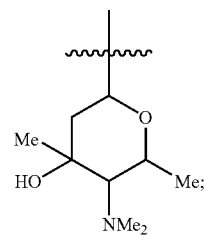

Z is selected from the group consisting of —$NH_2$ and

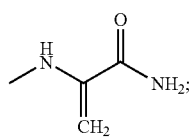

$R^1$ is selected from the group consisting of

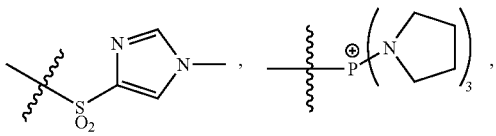

hydrogen, —P(O)$A^1A^2$, —C(O)$C_{1-6}$alkyl, —C(O)aryl, —C(O)NH$C_{1-6}$alkyl, —C(O)NHaryl, —(CH$_2$CH$_2$O)$_m$Me, —$C_{1-6}$alkenyl, —$C_{1-6}$alkynyl, and —$C_{1-6}$alkyl; wherein said $C_{1-6}$alkyl is optionally substituted by one to six hydroxy or optionally substituted by one to two same or different substituents selected from the group consisting of (a)–(i):

(a) CO$_2$R$^3$;
(b) CONR$^4$R$^5$;
(c) OP(O)A$^1$A$^2$;
(d) SO$_3$H;
(e) —O(CH$_2$)$_n$SiR$^6_3$;
(f) heteroalicyclic selected from the group consisting of pyrrolidinyl, piperidinyl, piperazinyl, and morpholinyl;
(g) cyano;
(h) epoxy; and
(i) aryl;

and provided that $R^1$ and $R^2$ are not simultaneously H;

$R^2$ is selected from the group consisting of

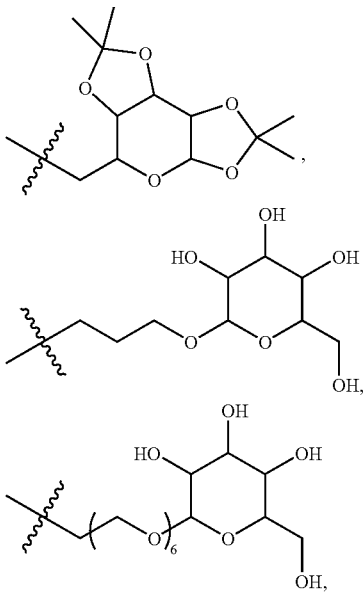

hydrogen, —P(O)A$^1$A$^2$, —SO$_3$H, —C(O)C$_{1-6}$alkyl, —C(O)CH═CHCO$_2$R$^3$, —C(O)aryl, —C(O)N(H)(C$_{1-6}$alkyl-T), —C(O)N(Me)(C$_{1-6}$alkyl-T), —(CH$_2$CH$_2$O)$_p$H, —(CH$_2$CH$_2$O)$_q$Me, —C$_{1-6}$alkenyl, —C$_{1-6}$alkyl and —C$_{1-6}$alkynyl; wherein said —C$_{1-6}$alkyl is optionally substituted by one to six hydroxy or optionally substituted by one to two same or different substituents selected from the group consisting of (j)–(v):

(j) halo;
(k) CO$_2$R$^3$;
(l) CONR$^4$R$^5$;
(m) OP(O)A$^1$A$^2$;
(n) P(O)A$^1$A$^2$;
(o) SO$_3$H;
(p) —O(CH$_2$)$_r$SiR$^6_3$;
(q) heterocyclic or heteroalicyclic selected from the group consisting of pyrrolidinyl, piperidinyl, piperazinyl, morpholinyl, imidazolyl, and pyridyl;
(r) cyano;
(s) azido;
(t) aryl;
(u) NR$^4$R$^5$; and (v)

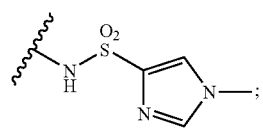

$R^3$ is selected from the group consisting of hydrogen, C$_{1-6}$alkyl, allyl, benzyl, 2-hydroxyethyl, and 2-tetrahydropyranyl;

$R^4$ and $R^5$ are each independently selected from the group consisting of hydrogen, C$_{1-6}$alkyl, CH$_2$CN, CH$_2$CH$_2$NH(t-butyloxycarbonyl), C(═NH)NH$_2$ and SO$_2$N(C$_{1-6}$alkyl)$_2$; or $R^4$ and $R^5$ taken together with the nitrogen to which they are attached form a heterocyclic or heteroalicyclic selected from the group consisting of pyrrolidinyl, piperidinyl, piperazinyl, morpholinyl, imidazolyl, and pyridyl;

$R^6$ is selected from C$_{1-6}$alkyl and phenyl;

$A^1$ and $A^2$ are each independently selected from the group consisting of hydrogen, —C$_{1-6}$alkyl, —OC$_{1-6}$alkyl, benzyloxy, 2-chloroethoxy, and hydroxy;

T is selected from the group consisting of hydrogen, —OH, —(CH$_2$CH$_2$O)$_s$H, —(CH$_2$CH$_2$O)$_t$CH$_3$ and —NR$^4$R$^5$;

m, n, p, q, r, s and t are independently 1–6; and aryl consists of a phenyl group optionally substituted with halo or —CO$_2$R$^3$.

In a preferred embodiment, Z is

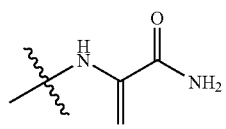

In another preferred embodiment, Z is —NH$_2$.
In another preferred embodiment, Z is

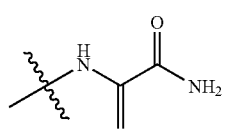

and includes the following groups (a)–(q):
(a) $R^1$ and $R^2$ are CH$_3$;
(b) $R^1$ and $R^2$ are P(O)(CH$_3$)OH;
(c) $R^1$ and $R^2$ are CH$_2$OP(O)(OH)$_2$;

(d) $R^1$ is $P(O)(CH_3)OH$ and $R^2$ is H;
(e) $R^1$ is

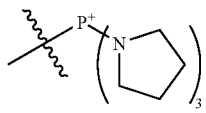

and $R^2$ is H;
(f) $R^1$ is H and $R^2$ is $P(O)(CH_3)OH$;
(g) $R^1$ is H and $R^2$ is $CH_2CONH_2$;
(h) $R^1$ is H and $R^2$ is $CH_2CO_2CH_3$;
(i) $R^1$ is H and $R^2$ is $CH_2CH_2CH_2SO_3H$;
(j) $R^1$ is H and $R^2$ is $CH_2P(O)(OEt)_2$;
(k) $R^1$ is H and $R^2$ is $CH_2OP(O)(OH)_2$;
(l) $R^1$ is H and $R^2$ is $CH_2CH_2Cl$;
(m) $R^1$ is H and $R^2$ is

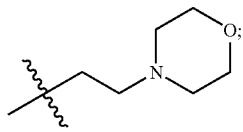

(n) $R^1$ is H and $R^2$ is $CH_3$;
(o) $R^1$ is H and $R^2$ is $CONH(CH_2CH_2O)_4H$;
(p) $R^1$ is H and $R^2$ is

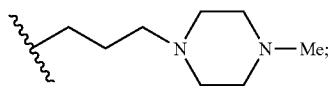

and
(q) $R^1$ is H and $R^2$ is

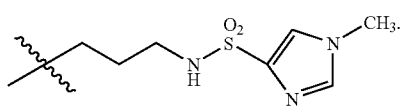

In another preferred embodiment, Z is —$NH_2$.
$R^1$ is H and $R^2$ is $CH_2CH_2$ $CH_2SO_3H$.

Another preferred embodiment includes a pharmaceutical composition which comprises a therapeutically effective amount of a compound I, including pharmaceutically acceptable salts thereof, and a pharmaceutically acceptable carrier, adjuvant or diluent.

Another preferred embodiment includes a method of treating or preventing bacterial or mycobacterial infection comprising administering to a mammal in need thereof a therapeutically effective amount of a compound I, including pharmaceutically acceptable salts thereof. More preferably, the bacterial infection is caused by a Gram-positive bacteria or mycobacterium. Still more preferably, this Gram-positive bacterial infection or mycobacterial infection is caused by a member selected from the group consisting of methicillin-resistant *Staphylococcus aureus*, vancomycin-resistant *Staphylococcus aureus*, vancomycin-resistant *Enterococcus faecalis,* vancomycin-resistant *Enterococcus faecium,* penicillin-resistant *Streptococcus pneumoniae* and *Mycobacteria tuberculosis.*

DETAILED DESCRIPTION OF THE INVENTION

The present invention comprises compounds of Formula I, including pharmaceutically acceptable salts thereof useful in treating bacterial infection.

Physiologically acceptable salts of compounds I disclosed herein are within the scope of this invention. The term "pharmaceutically acceptable salt" as used herein and in the claims is intended to include nontoxic base addition salts. Suitable salts include those derived from organic and inorganic acids such as, and without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

The compounds of the present invention may have chiral centers other than those centers whose stereochemistry is depicted in Formula I, and therefore may occur as mixtures of diastereomers or as single diastereomers. It is understood that all such isomeric forms, and any mixtures thereof, are included in the present invention. For example, the group W in a compound of Formula I is a sugar residue of the formula

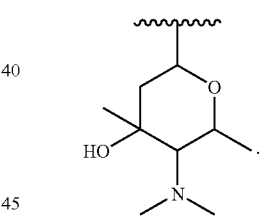

It is to be understood to encompass racemic forms of the sugar residue as well as chiral forms of the sugar residue such as

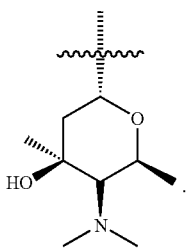

In addition, some of the compounds of the present invention may form solvates with water or common organic solvents. Such solvates are within the scope of this invention.

Formula I compounds can be prepared by using the methods shown in Scheme 1. Starting material compounds of Formula II, where Z is

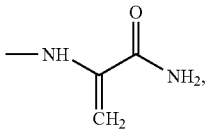

are produced according to the methods described by J. E. Leet et al in U.S. Pat. No. 6,218,398 (issued Apr. 17, 2001), which is incorporated in its entirety by reference herein; and by W. Li et al in PCT Appl. WO 02/13834 (published Feb. 2, 2002), where Z is —$NH_2$.

PCT WO 02/13834 in Examples 1, 2 and 3 discloses the preparation of Nocathiacin IV, the starting material II herein, where Z is —$NH_2$. The Nocathiacin IV structure is shown below:

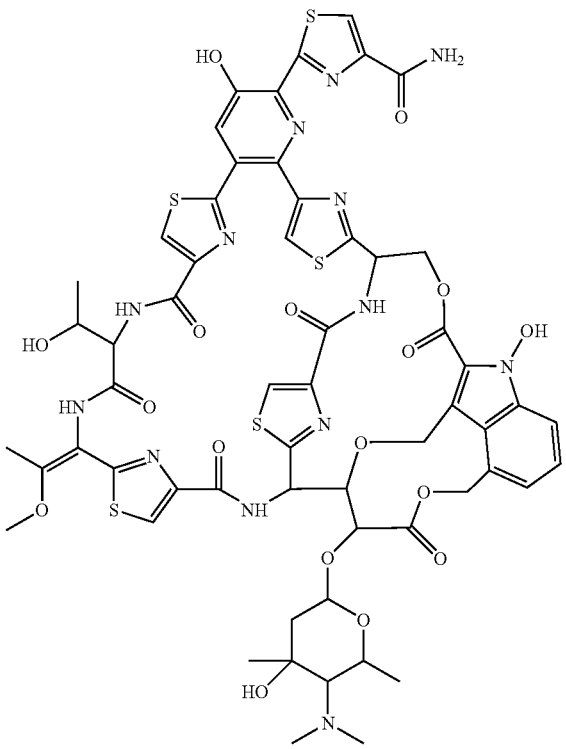

Examples 1, 2 and 3 (referred to below as Preparations 1, 2 and 3) are herein repeated below.

PREPARATIONS

Preparation 1

Synthesis by Biotransformation and Isolation of Nocathiacin IV

To 200 mL of a solution of nocathiacin I in DMF (1 mg/mL) in a 500 mL flask, was added 400 mg of protease from *Streptomyces griseus* (Sigma, Cat#P5147). The flask was incubated at 27° C. and 200 rpm for 45 hours. The reaction mixture from three flasks was pooled and centrifuged (3000 rpm, 15 min). The supernatant was evaporated in vacuo to dryness in a rotary evaporator to yield 0.76 g of brown residue.

10 mL of DMF was added to the brown residue and the insoluble material was removed by centrifugation (13000 rpm, 5 min). The resulting solution was subjected to preparative HPLC using the Beckman System Gold preparative HPLC system with an YMC Pro-C18 column (20 mmID× 250 mm length, 5□□ particle size, 120 Å pore size). Elution flow rate was 10 mL/min. In each run, sample (1 to 2 mL) was loaded onto the column at 1 mM HCl (solvent A)—acetonitrile (solvent B) 70/30 v/v and separated using the following gradient program: 30% B, 12 min; 30% to 35% B (or 34% or 33% B) linear gradient, 1 min; 35%(or 34% or 33% B), 30 min. Detection (UV) was at 330 nm. The fractions containing nocathiacin IV were assayed with analytical HPLC and pooled. The nocathiacin IV solution was evaporated in vacuo to a small volume, then was frozen and lyophilized. A total of 258 mg of nocathiacin IV was obtained as the hydrochloride salt.

| Physico-Chemical Properties of Nocathiacin IV (Hydrochloride Salt) | |
|---|---|
| Description: | shiny yellow granular powder |
| Molecular Formula: | $C_{58}H_{57}N_{13}O_{17}S_5$—HCl |
| Molecular Weight: | 1367 |
| Formula Weight: | 1403 |
| Mass Spectrum: | HR-ESIMS [M+H]$^+$ m/z 1368.26927 |
| | ESI-MS/MS fragmentation ions: m/z 1197, 1179, 1135 |
| Infrared Spectrum: | Major IR Bands (cm$^{-1}$) 3427, 1650, 1536, 1474, 1208, 1128, 604. |
| Ultraviolet Spectrum: | $\lambda_{max}$ (MeOH) nm 221, 294, 359 (log $\epsilon$ 4.84, 4.45, 4.22). |
| Circular Diebroism: | CD $\lambda$ nm ($\Delta\epsilon$) (MeOH) 357(+6.3), 306(−7.4), 266(+23.7), 239(−51.8). |
| HPLC (Rt) | 8.8 min; (as described in the Analytical HPLC section). |
| $^1$H-NMR | Observed Chemical Shifts (relative to DMSO-$d_6$ signal $\delta$ 2.49): |
| | $\delta$ 10.79 (1H, s), 9.08 (1H, s), 8.62 (1H, s), 8.57 (1H, br), 8.55 (1H br), 8.51 (1H, s), 8.44 (1H, s), 8.22 (1H, s), 7.98 (1H, s), 7.86 (1H, s), 7.84 (1H, m), 7.72 (1H, d, J=8.4 Hz), 7.67 (1H, s), 7.34 (2H, br), 7.18 (1H, d, J=6.6 Hz), 6.50 (4H, s), 6.00 (1H, d, J=12.0 Hz), 5.72 (2H, m), 5.21 (1H, m), 5.05 (1H, br), 5.03 (1H, s), 4.96 (1H, d, J=5.3 Hz), 4.78 (1H, d, J=10.2 Hz), 4.52 (1H, d, J=10.9 Hz), 4.29 (1H, d, J=9.6 Hz), 4.24 (1H, m), 4.13 (1H, d, J=10.5 Hz), 4.03 (1H, d, J=9.3 Hz), 3.89 (3H, s), 3.87 (1H, m), 3.07 (1H, br), 2.86 (6H, s), 2.47 (1H, m), 2.11 (1H, br), 1.98 (3H, s), 1.92 (1H, d, J=10.2 Hz), 1.59 (3H, s), 1.51 (1H, m), 1.14 (3H, br), 0.79 (3H, d, J=6.4 Hz). |
| $^{13}$C-NMR | Observed Chemical Shifts (relative to DMSO-$d_6$ signal $\delta$ 39.6): |
| | $\delta$ 171.6, 168.2, 168.0, 167.8, 167.0, 163.7, 163.3, 161.7, 161.6, 161.1, 160.6, 160.4, 158.9, 154.3, 151.1, 150.8, 149.7, 148.8, 145.6, 143.3, 135.0, 134.4, 130.3, 128.0, 127.6, 126.9, 126.4, 126.3, 125.8, 125.7, 124.0, 123.2, 120.0, 119.4, 112.9, 111.2, 109.6, 94.7, 79.2, 71.0, 68.9, 67.7, 66.8, 65.3, 64.6, 63.2, 63.1, 56.2, 55.5, 50.1, 50.0, 46.4, 44.0, 38.9, 30.3, 17.9, 17.6, 13.1. |

Preparation 2

Synthesis of Nocathiacin IV by Chemical Methods

A suspension of nocathiacin 1 (3.1 g, 2.1 mmol) in THF (10 mL) was treated with hydroiodic acid (57% in water, 0.5 mL, 3.8 mmol) and methyl iodide (1.0 mL, 16 mmol). The reaction mixture was heated in a sealed tube at 45° C. for 16 h. The reaction mixture was then allowed to cool to room temperature. Diethyl ether (25 mL) was then added to the mixture, and the resulting yellow precipitate was collected by filtration, washed with diethyl ether (3×25 mL) and dried under reduced pressure to afford 3.4 g of crude material containing Nocathiacin IV (82% purity) as the HI salt (88% crude yield).

A portion of the crude nocathiacin IV (517 mg) was purified by reverse phase chromatography on a preparative C-18 column using $CH_3CN/H_2O$/TFA as mobile phase (gradient elution 20% $CH_3CN$/78% $H_2O$/2% TFA to 35% $CH_3CN$/63% $H_2O$/2% TFA). Nocathiacin IV as the TFA salt was isolated (180 mg, 93% pure). This material was used for characterization and comparison with the biotransformation product.

| Physico-Chemical Properties of Nocathiacin IV (Trifluoroacetic acid salt) | |
|---|---|
| Description: | yellow granular powder |
| Molecular Formula: | $C_{58}H_{57}N_{13}O_{17}S_7$-TFA |
| Molecular Weight: | 1367 |
| Formula Weight: | 1482 |
| Mass Spectrum: | HR-ESIMS $[M+H]^+$ m/z 1368.269 |
| | ESI-MS/MS fragmentation ions: m/z 1197, 1179, 1153, 1135, 1117, 719 |
| Infrared Spectrum: | Major IR Bands ($cm^{-1}$) 3438, 1676, 1536, 1475, 1204, 1132, 596 |
| Ultraviolet Spectrum: | $\lambda_{max}$ (MeOH) nm 219, 294, 359 |
| Circular Dichroism: | CD λ nm (Δε) (MeOH) 3.55 (+5.6), 305 (−6.3), 265.5 (+21.0), 239 (−43.5), 210.5 (+29.9) |
| HPLC (Rt): | 8.8 min: (as described in the Analytical HPLC section). A sample of this semi-synthetic material was co-injected with a sample of the biotransformation product and they had identical retention times. |
| $^1$H-NMR: | Observed Chemical Shifts (relative to DMSO-$d_6$ signal δ 2.50): |
| | δ 10.84 (1H, s), 10.78 (1H, s), 9.11 (1H, s), 8.65 (1H, s), 8.59 (1H, br), 8.57 (1H, br), 8.54 (1H, s), 8.46 (1H, s), 8.22 (1H, s), 7.99 (1H, s), 7.89 (1H, s), 7.86 (1H, d, J=11 Hz), 7.75 (1H, d, J=8.5), 7.71 (1H, s), 7.37 (2H m), 7.19 (1H, d, J=7.0 Hz), 6.02 (1H, d, J=12.0 Hz), 5.76 (1H, dd, J=11.2 Hz, 4.2 Hz), 5.72 (1H, d, J=10 Hz), 5.23 (1H, m), 5.05 (3H, m), 4.79 (1H, d, J=10.5), 4.53 (1H, d, J=11 Hz), 4.30 (1H, d, J=9.5 Hz), 4.25 (1H, m), 4.16 (3H, d, J=0.5 Hz), 4.05 (1H, dd, J=9.5 Hz, 1.5 Hz), 3.91 (1H, s), 3.87 (1H, s), 3.13 (1H, br), 2.88 (6H, m), 2.50 (1H, br), 2.12 (1H, m), 2.0 (3H, s), 1.94 (1H, d=14.5 Hz), 1.60 (3H, s), 1.52 (1H, d, J=7 Hz), 1.17 (3H, br), 0.8 (3H, d, J=7.0 Hz) |
| $^{13}$C-NMR | Observed Chemical Shifts (relative to DMSO-$d_6$ signal δ 39.6) |
| | δ 171.3, 168.0, 167.8, 167.6, 166.8, 163.6, 163.1, 161.4, 160.9, 160.4, 160.2, 158.7, 154.1, 150.9, 150.6, 149.5, 148.6, 145.39, 143.1, 134.8, 134.2, 130.1, 127.8, 127.4, 126.7, 126.3, 126.1, 125.6, 125.5, 123.8, 123.0, 119.8, 119.3, 112.7, 111.0, 109.4, 94.5, 78.9, 72.2, 70.9, 68.8, 67.5, 66.3, 65.1, 64.4, 63.0, 62.7, 56.0, 49.9, 49.7, 46.5, 42.1, 38.1, 30.0, 17.7, 17.3, 12.9 |

Preparation 3

Synthesis of Nocathiacin IV (Free Base)

To a solution of nocathiacin IV-TFA salt (compound of Preparation 2, 35 mg) in THF/$CH_3CN$ (3.5 mL, 6:1) was added 1,3-2-diazaphosphorine on polystyrene (26 mg, 2.3 mmol/g) and the mixture was stirred at 25° C. for 30 minutes. The resin-bound base (1,3-2-diazaphosphorine on polystyrene) was then removed by filtration. The filter cake was washed with MeOH, THF, $CH_3CN$ and $H_2O$. The filtrate was then concentrated under reduced pressure in order to remove volatiles. The resulting solution was frozen and lyophilized to afford 24 mg of nocathiacin IV as the free base.

| Physico-Chemical Properties of Nocathiacin IV (free base) | |
|---|---|
| Description: | yellow granular powder |
| Molecular Formula: | $C_{58}H_{57}N_{13}O_{17}S_5$ |
| Molecular Weight: | 1367 |
| Formula Weight: | 1367 |
| Mass Spectrum: | HR-ESIMS $[M+H]^+$ m/z 1368.267 |
| | ESI-MS/MS fragmentation ions: m/z 1368.0, 1196.9, 1153.1, 1134.8, 1116.9, 719.1 |
| HPLC (Rt): | 8.8 min: (as described in the Analytical HPLC section). A sample of the free base had the same retention time as the semi-synthetic material (compound of Preparation 2) and with a sample of the biotransformation product (compound of Preparation 1). |
| $^1$H-NMR: | Observed Chemical Shifts (relative to DMSO-$d_6$ signal δ 2.50): |
| | δ 10.74 (1H, s), 9.10 (1H, s), 8.65 (1H, br), 8.60 (1H, s) 8.58 (1H, br), 8.51 (1H, s), 8.40 (1H, s), 8.25 (1H, s), 7.99 (1H, s), 7.89 (1H, s), 7.88 (1H, d, J=11.5 Hz), 7.73 (1H, m), 7.70 (1H, br), 7.37 (2H m), 7.18 (1H, d, J=7.0 Hz), 6.00 (1H, d, J=12.0 Hz), 5.74 (1H, dd, J=11.0 Hz, 4.5 Hz), 5.69 (1H, d, J=8 Hz), 5.22 (1H, m), 5.05 (2H, m), 5.00 (1H, m), 4.77 (1H, d, J=10.5), 4.52 (1H, d, J=11 Hz), 4.30 (1H, d, J=9.5 Hz), 4.26 (1H, s), 4.15 (1H, m), 4.03 (1H, m), 3.98 (3H, br), 3.80 (1H, m), 3.47 (1H, m), 3.18 (1H, m), 2.52 (6H, m), 2.23 (1H, m), 1.99 (3H, s), 1.83 (2H, m), 1.63 (1H, m), 1.45 (3H, s), 1.32 (1H, m), 1.17 (3H, br), 0.85 (3H, d, J=7.5 Hz). |

Conversion of formula II starting compounds into final compounds I may be accomplished by a variety of methods known to organic chemists skilled in the art including alkyations, acylations, and phosphonylations. These methods generally use commercially available agents or agents readily made by one skilled in organic synthesis. The alkylations of the present invention are generally performed by treating a compound of formula II with an alkyl halide or sulfonate in a suitable solvent, such as N,N-dimethylformamide or dichloromethane, in the presence of a base with or without sodium iodide or a catalytic amount of tetra-n-butylammonium iodide. Suitable bases are well known to those skilled in organic chemistry and include organic bases such as triethylamine and phosphazine bases as well as inorganic bases such as potassium carbonate, sodium hydroxide, and cesium carbonate. Acylations are generally performed by treating formula II compounds with an acylating agents in a suitable solvent, such as N,N-dimethylformamide or dichloromethane, and sometimes require the use of a suitable base as above. Suitable acylating agents include carboxylic acid halides and anhydrides, alkylchloroformates, and isocyanates. Phosphonylations are performed by treating formula II compounds with alkylphosphonic dihalides or monohalides in a suitable solvent such as N,N-dimethylformamide or dichloromethane. Examples of these transformations will be given in the Specific Embodiments section.

Various Formula I compounds can also be used as synthetic intermediates and elaborated into additional examples of Formula I. The elaborations, while generating specific examples, are general in nature and are adaptable by one skilled in organic synthesis. Examples of these transformations will also be given in the Specific Embodiments section and will provide additional experimental detail.

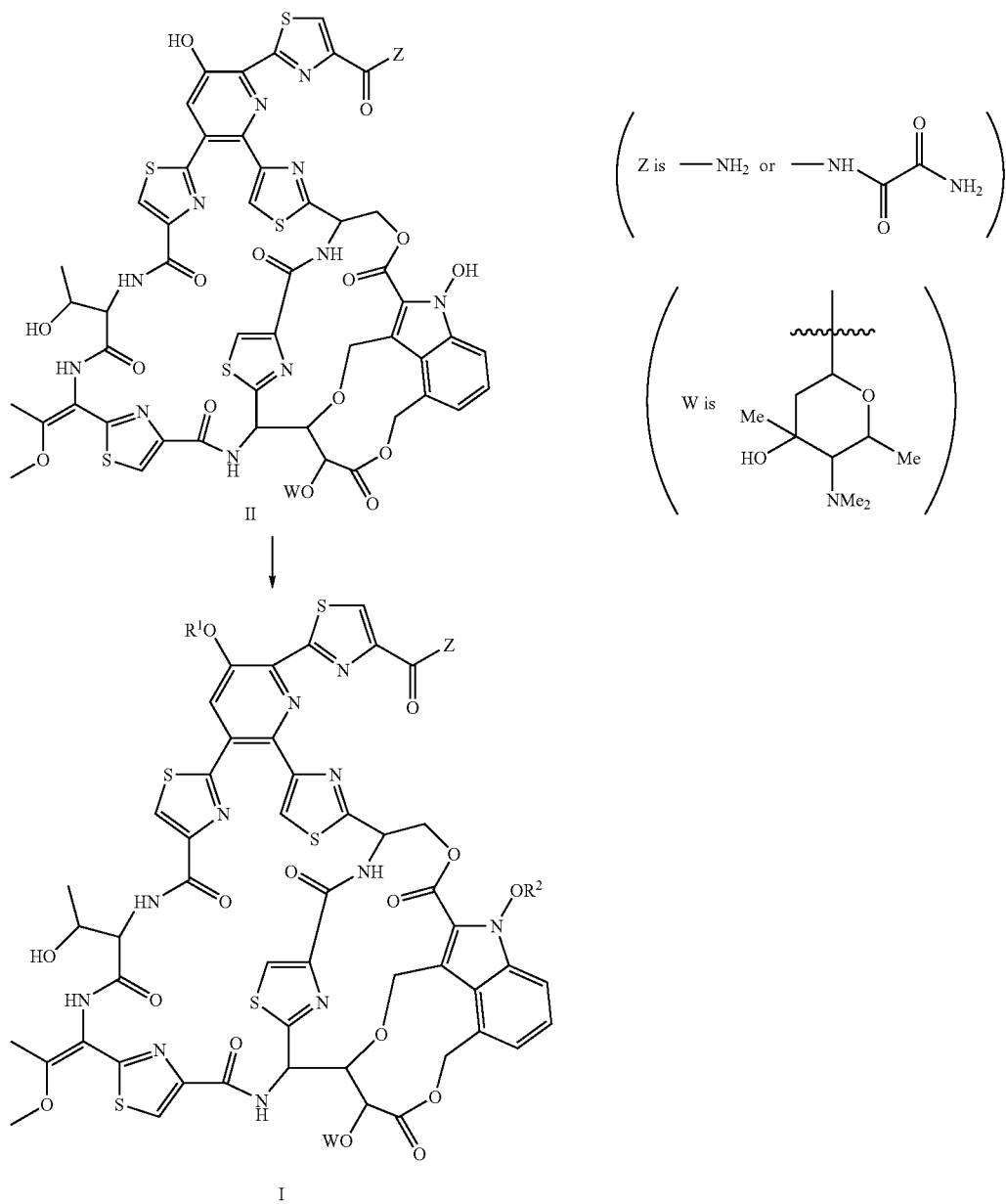

The compounds of formula I demonstrate potent antimicrobial activity against bacteria and mycobacteria such as *Staphylococcus aureus, Staphylococcus pneumoniae,* and *Enterococcus faecalis.* The antimicrobial activity includes action against Gram-positive bacteria including some multiresistant strains. Thus, the invention provides methods for the treatment of infectious diseases.

When the compounds of Formula I are employed as pharmaceutical compositions for the treatment of bacterial infections, they may be combined with one or more pharmaceutically acceptable carriers, for example, solvents, diluents, and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT (butylated hydroxy toluene), and BHA (butylated hydroxy anisole).

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. The abbreviations and symbols used in the examples are standard in the art and will be understood by someone skilled in the art.

General Procedure for O-alkylations

To a stirred solution of nocathiacin I or II (1.0 equivalent) in an appropriate volume of solvent (preferred solvents: N,N-dimethylformamide, tetrahydrofuran, dichloromethane, dimethylsulfoxide, acetonitrile, water) was added 1 to 3 equivalents of inorganic base (sodium hydride, cesium carbonate, sodium carbonate, potassium carbonate, sodium hydroxide) or organic base (triethylamine, diisopropylethylamine, phosphazene base such as tert-butylimino-tri(pyrrolidino)phosphorane (BTPP), 2-tert-butylimino-2-diethylamino-1,3-dimethyl-perhydro-13,2-diazaphosphorine (BEMP), BEMP on polystyrene) at room temperature with or without sodium iodide (up to 4 equivalent) or a catalytic amount (ca. 0.5 equivalent) of tetra n-butylammonium iodide. An alkyl halide, triflate, or mesylate (1.5 to 4.0 equivalents) was added and the reaction was stirred until nocathiacin was consumed. The solvent was removed under vacuum and the resulting residue was purified by using preparative HPLC (high pressure liquid chromatography) with methanol/water or MPLC (medium pressure liquid chromatography) on preparative C18 (ODS-A, S-75 μm) column with acetonitrile/water as eluent. The fractions containing products were combined, concentrated, and freeze-dried to afford the desired products as their TFA or HCl salt.

General Procedure for Carbamate Synthesis

To a stirred solution of nocathiacin I or II (1.0 equivalent) in an appropriate volume of solvent (preferred solvents: N,N-dimethylformamide, tetrahydrofuran, dichloromethane, dimethylsulfoxide, acetonitrile) was added up to 3 equivalents of organic base (triethylamine, disopropylethylamine, phosphazene base such as tert-butylimino-tri (pyrrolidino)phosphorane (BTPP), 2 -tert-butylimino-2-diethylamino-1,3-dimethyl-perhydro-13,2-diazaphosphorine (BEMP) on polystyrene at room temperature. After stirring for 5 to 10 minutes, the reaction mixture was cooled in an ice-water bath and 4-nitrophenyl chloroformate (up to 4 equivalents) was added and stirred for additional 10 minutes. To this solution was added an amine (1–4 equivalents). The reaction was stirred until reaction was complete and then quenched with 1N HCl. If the reaction mixture turned heterogeneous upon addition of aq. HCl, it was brought back to solution by adding additional DMF or methanol. The final clear solution was purified by MPLC on preparative C18 (ODS-A, S-75 μm) using acetonitrile-water. The fractions containing desired product were combined, concentrated, and freeze-dried to give yellow powders.

General Procedure for the Synthesis of Phosphonates

To a stirred solution/suspension of nocathiacin I or II (1.0 equivalent) in an appropriate volume of solvent (preferred solvents: N,N-dimethylformamide, tetrahydrofuran, dichloromethane, dimethylsulfoxide, acetonitrile) was added up to 3 equivalents of organic base (triethylamine, disopropylethylamine, phosphazene base such as tert-butylimino-tri (pyrrolidino)phosphorane (BTPP), 2-tert-butylimino-2-diethylamino-1,3-dimethyl-perhydro-13,2-diazaphosphorine (BEMP), on polystyrene at 0° C. Alkylphosphonic dichloride (1 to 3 equivalents) was added and the mixture was stirred at 0° C. until the reaction was complete. The homogeneous reaction mixture was quenched with saturated aqueous sodium bicarbonate (20 mL) and concentrated. The residue was suspended in water (300 mL) and the remaining solids were filtered. The aqueous solution was purified by chromatography (preparative C18, ODS-A, S-75 μm, acetonitrile/water). The fractions containing desired product were combined, concentrated, and freeze-dried.

General Procedure for the Preparation of Esters

To a stirred solution/suspension of nocathiacin (1.0 equivalent) in an appropriate volume of solvent (preferred solvents: N,N-dimethylformamide, tetrahydrofuran, dichloromethane, dimethylsulfoxide, acetonitrile, pyridine) was added up to 3 equivalents of inorganic base (sodium bicarbonate, sodium carbonate, cesium carbonate, potassium bicarbonate, potassium carbonate) or organic base (pyridine, triethylamine, disopropylethylamine, phosphazene base such as tert-butylimino-tri(pyrrolidino)phosphorane (BTPP), 2-tert-butylimino-2-diethylamino-1,3-dimethyl-perhydro-13,2-diazaphosphorine (BEMP), BEMP on polystyrene) at 0° C. An acid chloride or anhydride (1 to 3 equivalents) was added and the mixture was stirred until the reaction was complete. Sometimes warming the reaction from room temperature to reflux was necessary. The crude reaction was evaporated to dryness, and the resulting light yellow residue was further purified by prep HPLC or MPLC by chromatography (preparative C18, ODS-A, S-75 μm, acetonitrile/water or methanol/water). The fractions containing desired product were combined, concentrated, and freeze-dried.

EXAMPLE 1

Formula I: $R^1=CH_3$, $R^2=H$, $Z=NHC(=CH_2)CONH_2$

A solution of nocathiacin I (282 mg, 0.196 mmol) in anhydrous N,N-dimethylformamide (1 ml) was treated with tert-butylimino-tri(pyrrolidino)phosphorane (BTPP) (0.120 ml, 0.392 mmol) at room temperature for 3 min. Di-tert-butyl dicarbonate (0.046 ml, 0.196 mmol) was added and the reaction mixture was stirred for 10 min until the indole hydroxy group had been protected as the corresponding tert-butyl carbonate. Methyl iodide (0.012 ml, 0.196 mmol) was then added and the reaction was monitored by HPLC. After 2 h, conversion to the methyl ether was about 70%. An additional equiv. of methyl iodide (0.012 ml, 0.196 mmol) was then added and the reaction mixture was stirred at room temperature overnight. 1N HCl (0.3 ml) was then added and the reaction mixture was concentrated in vacuo to remove the N,N-dimethylformamide. The crude residue was dissolved in water/acetonitrile/methanol and treated with trifluoroacetic acid at room temperature until HPLC monitoring showed complete deprotection of the indole hydroxy group. The resulting solution was then purified using MPLC on a preparative C-18 column using acetonitrile/water as eluent. The fractions containing the desired product were combined and concentrated in vacuo to remove most of the acetonitrile. The residue was frozen and lyophilized to provide the product as the TFA salt (40.5 mg, 14% yield): $^1$H NMR (500 MHz, DMSO-$d_6$): δ 10.8 (1H, s), 10.3 (1H, s), 9.10 (1H, s), 8.68 (1H, s), 8.59 (1H, d, J=9.2 Hz), 8.54 (1H s), 8.54 (1H, s), 8.22 (1H, s), 8.14 (1H, s), 8.05 (1H, s), 7.92 (1H, s), 7.86 (1H, d, J=10.7 Hz), 7.76 (1H, d, J=8.45 Hz), 7.68 (1H, s), 7.35 (2H, dd, J=8.3, 7.3 Hz), 7.19 (1H, d, J=7.35 Hz), 6.51 (1H, s), 6.03 (1H, d, J=12.5 Hz), 5.75 (1H, s), 5.72 (2H, m), 5.21 (1H, m), 5.06 (2H, m), 4.79 (1H, d, J=10.5 Hz), 4.54 (1H, d, J=11.5 Hz), 4.30 (1H, d, J=9.6 Hz), 4.26 (1H, m), 4.20 (3H, s), 4.16 (1H, d, J=9.7 Hz), 4.05 (1H, d, J=9.7 Hz), 3.91 (3H, s), 3.13 (1H, s), 2.87 (6H, br), 2.47 (1H, m), 2.12 (1H, m), 2.00 (3H, s), 1.94 (1H, d, J=14.5 Hz), 1.60 (3H, br), 1.23 (1H, m), 1.16 (3H, br), 0.80 (3H, d, J=6.9 Hz). HRMS (ES) calcd. for $C_{62}H_{63}S_5N_{14}O_{18}$ (MH+): 1451.305; found 1451.309.

EXAMPLE 2

Formula I: $R^1$=1-(2,3-epoxy)propyl, $R^2$=H, $Z=NHC(=CH_2)CONH_2$

Sodium hydride (0.42 mmol) was added in one portion to a mixture of nocathiacin I (0.14 mmol) and activated 4 Å molecular sieves in tetrahydrofuran (5 ml) at 0° C. The mixture was stirred for 10 minutes, then epibromohydrin (0.21 mmol) was added. The reaction mixture was stirred for 10 hours at room temperature, then the solvent was removed at reduced pressure. Diethyl ether (5 ml) was added to precipitate a yellow solid which was further purified by preparative HPLC. The product containing fractions were frozen and lyophilized, resulting in 60 mg of the product as a yellow solid: MS (MH+)=1493.

EXAMPLE 3

Formula I: $R^1=CH_2CH(OH)CH_2OH$, $R^2=H$, $Z=NHC(=CH_2)CONH_2$

To a mixture of the compound of Example 2 (0.14 mmol) in acetonitrile (3 ml) and water (3 ml) at room temperature was added dilute aqueous HCl (0.1 N) until the pH was 3.0. The resulting clear solution was then stirred for approximately 1 h then the solvent was removed at reduced pressure. The resulting crude product was further purified by preparative HPLC. The product containing fractions were frozen and lyophilized, resulting in 20 mg of the product as a yellow solid: MS (MH+)=1511.

EXAMPLE 4

Formula I: $R^1=P^+(N\text{-pyrrolidine})_3$, $R^2=H$, $Z=NHC(=CH_2)CONH_2$

To a stirred solution of nocathiacin I (287 mg, 0.2 mmol), in N,N-dimethylformamide was added benzotriazole-1-yl-oxy-tris-pyrrolidino-phosphonium hexafluorophosphate (110 mg, 0.21 mmol) at room temperature. After 5 minutes, the reaction mixture was purified on the C18 reverse phase silica gel column using acetonitrile (10–35%)-water containing 0.01% HCl as an eluent. The fractions containing the product were combined, concentrated and freeze dried to give the product as a white powder. Obtained 0.21 g (60%) as HCl salt: $^1$H NMR (DMSO, 500 MHz): δ10.78 (1H, s), 9.77 (1H, s), 9.12 (1H, s), 8.75 (1H, s), 8.73 (1H, s), 8.66–8.58 (2H, m), 8.54 (1H, s), 8.21 (1H, s), 8.19 (1H, br s), 8.11 (1H, s), 8.09 (1H, s), 7.88 (1H, d, J=10.7 Hz), 7.75 (1H, d, J=8.6 Hz), 7.68 (1H, s), 7.39–7.35 (2H, m), 7.20 (1H, d, J=7.0 Hz), 6.51 (1H, s), 6.38 (1H, br s), 6.03 (1H, d, J=12.2 Hz), 5.80 (1H, s), 5.79–5.76 (1H, m), 5.71 (1H, d, J=10.1 Hz), 5.25–5.22 (1H, m), 5.09–5.02 (3H, m), 4.78 (1H, d, J=10.4 Hz), 4.50 (1H, d, J=11 Hz), 4.29 (1H, d, J=9.8 Hz), 4.26–4.24 (1H, m), 4.16 (1H, d, J=10.7 Hz), 4.06 (1H, d, J=8.2 Hz), 3.9 (3H, br s), 3.41–3.33 (10H, m), 3.12 (1H, s), 3.03–2.98 (6H, m), 2.83–2.90 (6H, m), 2.16–2.08 (1H, m), 1.99 (3H, s), 1.90–1.81 99H, m), 1.74–1.70 (6H, m), 1.60 93H, s), 1.15 (3H, br s), 0.80 (3H, d, J=6.7 Hz). LRMS (ES) calcd. for $C_{73}H_{83}N_{17}O_{18}PS_5$ (M+): 1676.4, found: 1676.5.

EXAMPLE 5

Formula I: $R^1=P(O)(CH_3)OH$, $R^2=H$,
Z=NHC(=CH_2)CONH_2

Nocathiacin I (1.0 g, 0.7 mmol) was dissolved in N,N-dimethylformamide (50 ml). Cesium carbonate (0.7 g, 2.1 mmol) was added and the mixture was stirred 30 min at room temperature. The mixture was cooled to 0° C., then methyl phosphonic dichloride (0.07 g, 0.54 mmol) was added and the mixture was stirred at 0° C. for 40 min. The reaction mixture was quenched with saturated aqueous sodium bicarbonate (6 ml) and the mixture was purified by chromatography (preparative C18, ODS-A, S-75 µm, 5%–15%–20%–40% acetonitrile/water) to provide the product (392 mg, 0.23 mmol, 33% yield) as sodium salt: MS (MH+) 1515.3; Anal. Calcd. For $C_{62}H_{63}N_{14}O_{20}PS_5 \cdot Na \cdot 0.5NaHCO_3 \cdot 7H_2O$: C, 43.98; H, 4.58; N, 11.49; P, 1.81; S, 9.39; Na, 2.02. Found: C, 44.06; H, 4.56; N, 11.42; P, 1.69; S, 9.06; Na, 2.09.

EXAMPLE 6

Formula I: $R^1=H$, $R^2=CH_3$,
Z=NHC(=CH_2)CONH_2

A solution of nocathiacin I (0.288 g, 0.20 mmol) in tetrahydrofuran (6 mL) and methanol (4 mL) was treated with (trimethylsilyl)diazomethane (2.0 M in Hexanes, 0.21 mL, 0.42 mmol). The reaction was stirred for 5 minutes under nitrogen atmosphere, followed by removal of solvent by rotary evaporator. The crude residue was loaded onto a C-18 reverse phase silica gel column (YMC Gel, 12 nm, S-75 µm) and purified by elution with 10% acetonitrile in water, increasing to 60% acetonitrile in water by stepwise gradient. Appropriate fractions were pooled and acetonitrile was removed by rotary evaporator. The aqueous solution was frozen and lyophilized, resulting in product (0.098 g, 0.068 mmol, 34% yield) as a yellow lyophilized solid: MS (MH+)=1451.

EXAMPLE 7

Formula I: $R^1=H$, $R^2=(CH_2)_3SO_3H$, Z=NHC(=CH_2)CONH_2

A solution of nocathiacin I (0.575 g, 0.40 mmol) in N,N-dimethylformamide (5 mL) was treated with sodium hydroxide (1.0 N solution, 0.84 mL, 0.84 mmol), and stirred at room temperature for approximately 5 minutes. The bright yellow solution was treated with 1,3-propane sultone (0.054 g, 0.44 mmol) and stirred for 6–8 hours. Solvent was removed in vacuo and the remaining residue was taken up in water (approximately 10 mL) and saturated sodium bicarbonate (1 mL). The solution was loaded onto a C-18 reverse phase silica gel column (YMC ODS, 12 nm, S-75 µm) and eluted with water, increasing to 30% acetonitrile in water by stepwise gradient. Product fractions were pooled and acetonitrile was removed by rotary evaporator. The aqueous solution was frozen for lyophilization. Product (0.234 g, 0.148 mmol, 37% yield) was obtained as a yellow lyophilized solid (sodium salt): MS (M–H)=1557.41. This compound was also prepared by use of BTPP as a base in DMF.

EXAMPLES 8 AND 9

Formula I: $R^1=H$, $R^2=CH_2C(O)NH_2$,
Z=NHC(=CH_2)CONH_2 and

Formula I: $R^1=CH_2C(O)NH_2$, $R^2=CH_2C(O)NH_2$,
Z=NHC(=CH_2)CONH_2

2-tert-Butylimino-2-diethylamino-1,3-dimethylperhydro-1,3,2-diazaphosphorine (BEMP) on polystyrene resin (0.28 mmol) was added to a solution of nocathiacin I (0.14 mmol) in N,N-dimethylformamide (5 ml) at room temperature. The mixture was stirred for 10 min, then 2-bromoacetamide (0.28 mmol) was added and the mixture was stirred at room temperature for 10 h. The mixture was filtered, and the filtrate was then concentrated at reduced pressure. The crude product thus obtained was further purified by preparative HPLC. The product containing fractions were frozen and lyophilized, resulting in 30 mg of the product (formula I: $R^1=H$, $R^2=CH_2C(O)NH_2$, Z=NHC(=CH_2)CONH_2) as a yellow solid: MS (MH+)=1494.

The same conditions above by the use of BEMP on polystyrene resin (0.56 mmol) and 2-bromoacetamide (0.56 mmol) provided 80 mg of the bis-product (formula I: $R^1=CH_2C(O)NH_2$, $R^2=CH_2C(O)NH_2$, Z=NHC(=CH_2)CONH_2) as a yellow solid: MS (MH+)=1551.

EXAMPLE 10

Formula I: $R^1=H$, $R^2$=4-carbo-(2-tetrahydropyranoxy)benzyl, Z=NHC(=CH_2)CONH_2 p-Toluenesulfonic acid monohydrate (34 mg, 0.178 mmol) was added to a cooled (ice/water bath) stirred mixture of 4-chloromethylbenzoic acid (3.03 g, 0.0178 mol) and dihydropyran (8.12 ml, 0.089 mol) in dichloromethane (85 ml). The ice bath was removed and stirring was continued at ambient temperature for 1 h. The reaction mixture was then concentrated in vacuo, then the residue was partitioned between diethyl ether and dilute aqueous sodium bicarbonate. The ethereal solution was washed (2× with brine), dried over anhydrous sodium sulfate and concentrated in vacuo to leave an oil (900 mg) which crystallized. The solid was chromatographed on silica (10 g) using chloroform as eluent to afford 2-tetrahydropyranyl 4-chloromethylbenzoate as colorless crystals (208 mg). MS (ESI) 254.

BEMP on polystyrene resin (182 mg, 0.42 mmol) was added to a stirred solution of nocathiacin I (287 mg, 0.2 mmol) in N,N-dimethylformamide (6 ml). Stirring was continued at 22° C. for 15 min then 2-tetrahydropyranyl-4-chloromethylbenzoate (80 mg, 0.3 mmol) was added. The reaction mixture was stirred for 3 h then triethylamine (56 µL, 0.42 mmol) was added and stirring was continued for 6 d. The reaction mixture was filtered, and the filtrate diluted with diethyl ether to precipitate the product (122 mg, 96% purity by HPLC), as a colorless solid: MS: (ESI) 1655.

EXAMPLE 11

Formula I: $R^1=H$, $R^2$=4-(carbohydroxy)benzyl,
Z=NHC(=CH_2)CONH_2

Hydrochloric acid (3 ml of 0.1N) was added to a stirred solution of the compound of Example 10 (92 mg) in tetrahydrofuran (40 ml). The mixture was stirred for 2 h at 22°

C. The resulting solid was collected and dried to afford the product as a yellow solid (50 mg, >95% purity by HPLC): MS (ESI): 1571.

EXAMPLE 12

Formula I: $R^1$=H, $R^2$=CH$_2$OP(O)(OH)$_2$, Sodium Salt and Ammonium Salt Forms, Z=NHC(=CH$_2$)CONH$_2$ A solution of nocathiacin I (5.85 g, 4.07 mmol) in N,N-dimethylformamide (35 ml) was treated at room temperature with tert-butylimino-tri(pyrrolidino)phosphorane (BTPP) (3.81 g, 12.21 mmol) and stirred for approximately 5 min. The mixture was then treated with O-chloromethyl-O',O''-di-tert-butyl phosphate (1.58 g, 6.10 mmol) and the reaction was stirred at room temperature for 5 h. The solvent was removed by rotary evaporator and the viscous oil residue was triturated with diethyl ether. The crude solid was collected by filtration. The solid was loaded onto a C-18 reverse phase column in 20% acetonitrile in water and purified, using a gradient system eventually reaching 45% acetonitrile in water. Fractions of product remaining in solution for 24 h underwent a loss of a tert-butyl group to provide the mono-tert-butyl intermediate. Appropriate fractions were collected and concentrated by rotary evaporator, then lyophilized to give the mono-tert-butyl intermediate (3.4 g). A portion of the intermediate (0.40 g, 0.25 mmol), used as is, was treated with 10% trifluoroacetic acid in dichloromethane (40 ml), stirred for approximately 5 min, followed by concentration by rotary evaporator. The oily residue was taken up in water (40 ml), concentrated sodium bicarbonate (to bring to pH 7.5–8), and acetonitrile as required to dissolve most of the insoluble material. The product was purified by C-18 reverse phase column chromatography, using a gradient system eventually reaching 20% acetonitrile in water. Appropriate fractions were combined and concentrated by rotary evaporator. The purified final product could then be isolated as the sodium salt form by lyophilization. To isolate as bis-ammonium salt form, the resulting aqueous solution from the previous column was passed again through a C-18 reverse phase chromatography column, with the aqueous portion of the mobile phase being replaced with 0.1 M ammonium acetate buffer. The gradient system eventually reached 40% acetonitrile in buffer. Appropriate fractions were combined and concentrated by rotary evaporator. The resultant aqueous buffer solution was dried by lyophilization to give the product (0.083 g, 0.053 mmol, 11% yield) as a pale yellow solid: $^1$H NMR (DMSO-d$_6$, 500 MHz); δ 10.06 (s, 1H), 9.12 (s, 1H), 8.96 (s, 1H), 8.67 (d, J=7.6, 1H), 8.52 (d, J=7.6, 1H), 8.51 (s, 1H), 8.26 (d, J=6.7, 1H), 8.25 (s, 1H), 8.05 (bs, 1H), 7.87 (s, 1H), 7.78 (d, J=10.97, 1H), 7.62 (bs, 1H), 7.32 (t, J=7.6, 1H), 7.19 (d, J=6.7, 1H), 7.12 (d, J=7.2, 1H), 6.38 (bs, 1H), 5.98 (d, J=11.9, 1H), 5.73 (s, 1H), 5.68 (d, J=9.0, 1H), 5.28–5.20 (m, 2H), 5.15 (m, 1H), 5.04 (d, J=13.3, 1H), 4.94 (d, J=3.8, 1H), 4.80 (d, J=10.5, 1H), 4.62 (d, J=10.5, 1H), 4.35 (t, J=9.5, 1H), 4.25 (m, 1H), 4.09 (d, J=10.0, 1H), 4.01 (d, J=9.0, 1H), 3.92 (s, 3H), 3.75 (m, 1H), 2.64 (s, 1H), 2.58 (s, 1H), 2.36 (s, 1H), 2.01 (s, 3H), 1.80 (d, J=15.2, 1H), 1.76 (s, 1H), 1.40 (bs, 3H), 1.14 (d, J=6.2, 3H), 0.54 (d, J=6.2, 3H); HRMS calculated for C$_{62}$H$_{63}$N$_{14}$O$_{22}$S$_5$P (MH+): 1547.266, found: 1547.268.

EXAMPLE 13

Formula I: $R^1$=H, $R^2$=CH$_2$CH$_2$Cl, Z=NHC(=CH$_2$)CONH$_2$

A solution of nocathiacin 1 (513 mg, 0.36 mmol) in anhydrous N,N-dimethylformamide (2 ml) was treated with BTPP (0.22 ml, 0.72 mmol) at room temperature for 3 min. Chloroethyl methanesulfonate (0.041 mg, 0.36 mmol) was added and the reaction mixture was stirred overnight. The solvent was removed in vacuo and the residue was dissolved in water/acetonitrile, treated with 1N HCl (0.72 ml, 0.72 mmol) and purified using MPLC on preparative C-18 column using acetonitrile/water as eluent. The fractions containing the desired product were combined and concentrated in vacuo to remove most of the acetonitrile. The residue was frozen and lyophilized to provide the product as the HCl salt (210 mg, 40% yield): HRMS (ES) calcd. for C$_{63}$H$_{64}$ClN$_{14}$O$_{18}$S$_5$ (MH+): 1499.281, found: 1499.283.

EXAMPLE 14

Formula I: $R^1$=H, $R^2$=—(CH$_2$)$_3$N$^1$(CH$_3$)$_3$, Z=NHC(=CH$_2$)CONH$_2$ A solution of nocathiacin I (262 mg, 0.18 mmol) in anhydrous N,N-dimethylformamide (1 ml) was treated with BTPP (0.114 ml, 0.36 mmol) at room temperature for 3 min. (3-Bromopropyl)trimethylammonium bromide (47 mg, 0.18 mmol) was added and the reaction mixture was stirred for 4 h at room temperature. 1N HCl (3 ml) was then added and the solution was concentrated in vacuo to remove the N,N-dimethylformamide. The residue was purified using MPLC on a preparative C-18 column using acetonitrile/water as eluent. The fractions containing the desired product were combined and concentrated in vacuo to remove most of the acetonitrile. The residue was then frozen and lyophilized to provide the product as the HCl salt (193 mg, 69% yield): $^1$H NMR (500 MHz, DMSO-d$_6$): δ 10.8 (1H, s), 10.0 (1H, s), 9.25 (1H, s), 8.86 (1H, m), 8.66 (1H, s), 8.59 (2H, br), 8.55 (1H, s), 8.28 (1H, s), 8.22 (1H, s), 8.13 (1H, br), 7.86 (1H, s), 7.74 (1H, d, J=10.0 Hz), 7.64 (1H, br), 7.55 (1H, d, J=10.0 Hz), 7.46 (1H, dd, J=10.0, 5.0 Hz), 7.31 (1H, d, J=10.0 Hz), 7.13 (1H, d, J=5 Hz), 6.39 (2H, br), 6.01 (1H, d, J=10 Hz), 5.89 (1H, m), 5.76 (1H, s), 5.71 (1H, d, J=10.0 Hz), 5.4 (1H, d, J=5.0 Hz), 5.32 (2H, s), 5.30 (2H, s), 5.09 (1H, m), 5.05 (1H, m), 4.83 (1H, dd, J=15.0, 10.0 Hz), 4.41 (1H, m), 4.11 (1H, dd, J=10.0, 5.0 Hz), 3.9 (3H, s), 3.87 (1H, m), 3.43 (9H, br), 3.17 (6H, br), 2.97 (1H, br), 2.87 (1H, br), 2.02 (2H, s), 1.82 (4H, m), 1.58 (3H, br), 1.24 (3H, br), 1.12 (1H, m), 0.78 (3H, d, J=5.0 Hz); HRMS (ES) calcd. for C$_{67}$H$_{74}$N$_{15}$O$_{18}$S$_5$$^+$ (M$^+$): 1536.394, found: 1536.389.

EXAMPLE 15

Formula I: $R^1$=H, $R^2$=C(O)NH(CH$_2$)$_3$CH$_3$, Z=NHC(=CH$_2$)CONH$_2$

Nocathiacin I (0.2874 g, 0.2 mmol) was dissolved in N,N-dimethylformamide (2 ml). Phosphazine base P$_1$-t-Butris-(tetramethylene) (BTPP, 0.2 ml, 0.6 mmol) was added and the mixture was stirred 10 min then cooled to 0° C. 4-Nitrophenylchloroformate (0.14 g, 0.7 mmol) was added and the mixture was stirred at 0° C. for 10 min. n-Butylamine (0.03 ml, 0.3 mmol) was added and the mixture was stirred at 0° C. for 15 min then quenched with 1N HCl (3 ml). N,N-dimethylformamide was added to dissolve solids and the mixture was purified by chromatography (preparative C18, ODS-A, S-75 μm, 20%–30% acetonitrile/water/ 0.5 mL 1N HCl/L) to yield the product as a yellow powder (0.0234 g, 7% yield): $^1$H NMR (DMSO, 500 MHz): δ 11.27 (s, 1H), 10.06 (s, 1H), 9.20 (s, 1H), 8.64 (m, 2H), 8.60 (s, 1H), 8.54 (s, 1H), 8.21 (s, 1H), 8.09 (s, 1H), 8.01 (m, 1H), 7.88 (m, 1H), 7.75 (m, 1H), 7.62 (s, 1H), 7.43 (m, 1H), 7.36 (m, 1H) 7.28 (m, 1H), 7.19 (m, 1H), 6.38 (s, 1H), 6.36 (s, 1H), 6.06 (m, 1H), 5.76 (s, 1H), 5.72 (m, 1H), 5.08, (m, 2H), 4.89, (m, 1H), 4.30 (m, 2H), 4.13 (m, 2H), 3.91 (s, 3H), 3.40 (m, 7H), 3.11 (m, 1H), 2.87 (m, 7H), 2.54 (m, 2H), 2.12 (m, 1H), 2.08 (s, 1H), 2.03 (m, 2H), 1.93 (d, J=15.0 Hz, 1H), 1.60 (s, 3H), 1.39 (m, 1H), 1.23 (m, 1H), 1.14 (m, 4H), 0.78 (m, 6H); LRMS (ESI+) m/z=1536.6. (ESI−) m/z=1534.58.

EXAMPLE 16

Formula I: $R^1$=H, $R^2$=C(O)NH(CH$_2$)$_3$-(4-methylpiperazin-1-yl), Z=NHC(=CH$_2$)CONH$_2$ Following the procedure for example 15 except using 1-(3-aminopropyl)-4-methylpiperazine (0.12 g, 0.6 mmol) in place of n-butylamine, the product was isolated as a yellow powder (0.1141 g, 41% yield): $^1$H NMR (DMSO, 500 MHz): δ 11.82 (bs, 1H), 11.36 (s, 1H), 10.06 (s, 1H), 9.21 (s, 1H), 8.92 (bs, 1H), 8.76 (s, 2H), 8.60 (s, 1H), 8.54 (s, 1H), 8.22 (s, 1H), 8.11 (s, 2H), 8.02 (m, 1H), 7.88 (m, 1H), 7.75 (d, J=10.0 Hz, 1H), 7.63 (s, 1H), 7.45 (s, 1H), 7.28 (d, J=5.0 Hz, 1H), 7.21 (m, 1H), 6.38 (s, 1H), 6.06 (d, J=10.0 Hz, 1H), 5.77 (s, 1H), 5.71 (m, 2H). 5.10 (s, 1H), 5.07 (s, 2H), 4.87 (bs, 1H), 4.35 (m, 1H), 4.26 (m, 1H), 4.11 (m, 2H), 3.92 (s, 2H), 3.86 (s, 1H), 3.59–3.30 (m, 15H), 3.10 (s, 3H), 2.88 (s, 6H), 2.77 (s, 3H), 2.13 (d, J=10.0 Hz, 1H), 2.04 (s, 3H), 1.92 (d, J=15.0 Hz, 1H), 1.84 (m, 1H), 1.59 (s, 3H), 1.13 (s, 3H), 0.77 (s, 3H); HRMS (ES) calcd. for $C_{70}H_{78}S_5N_{17}O_{19}$ (MH+): 1620.426. Found 1620.428.

EXAMPLE 17

Formula I: $R^1$=H, $R^2$=P(O)(CH$_3$)OH, Z=NHC(=CH$_2$)CONH$_2$

Nocathiacin I (1.0 g, 0.7 mmol) was dissolved in N,N-dimethylformamide (25 ml). Phosphazine base P$_1$-t-Bu-tris-(tetramethylene) (BTPP, 0.65 ml, 2.1 mmol) was added and the mixture was stirred for 5 min. The mixture was cooled to 0° C. and methylphosphonic dichloride (0.09 g, 0.7 mmol) was added then the mixture was stirred at 0° C. for 30 minutes. Saturated aqueous sodium bicarbonate (6 ml) was added followed by enough water to dissolve the resulting solids. The mixture was purified by chromatography (preparative C18, ODS-A, S-75 μm, 15% acetonitrile/water-30% acetonitrile/water) to yield the product as a yellow powder (0.083 g, 8% yield): $^1$H NMR (DMSO, 500 MHz): δ 11.42 (bs, 1H), 10.08 (s, 1H), 9.01 (s, 1H), 8.71 (s, 1H), 8.56 (s, 1H), 8.53 (s, 1H), 8.20 (s, 1H), 8.07 (bs, 1H), 7.91 (s, 1H), 7.88 (m, 1H), 7.83 (m, 2H), 7.61 (bs, 1H), 7.24 (t, J=7.5 Hz, 1H), 7.12 (d, J=10.0 Hz, 1H), 7.09 (d, J=10.0 Hz, 1H), 6.35 (s, 1H), 6.02 (d, J=15.0 Hz, 1H), 5.74 (s, 1H), 5.70 (d, J=10.0 Hz, 1H), 5.13 (d, J=5.0 Hz, 1H), 5.02 (m, 2H), 4.90 (d, J=10.0 Hz, 1H), 4.55 (d, J=10.0 Hz, 1H), 4.28 (d, J=10.0 Hz, 1H), 4.13 (m, 2H), 3.99 (d, J=10.0 Hz, 1H), 3.90 (s, 3H), 3.02 (m, 5H), 2.98 (m, 1H), 2.78 (m, 4H), 2.26 (m, 1H), 2.05 (m, 1H), 2.00 (s, 3H), 1.89 (d, J=15.0 Hz, 1H), 1.73 (m, 6H), 1.55 (m, 2H), 1.19 (s, 1H), 1.15 (m, 3H), 0.90 (d, J=15.0 Hz, 2H), 0.76 (m, 2H); HRMS (ES) calcd. for $C_{62}H_{64}PS_5N_{14}O_{20}$ (MH+): 1515.276, Found: 1515.272.

EXAMPLE 18

Formula I: $R^1$=$R^2$=CH$_3$, Z=NHC(=CH$_2$)CONH$_2$

Method a:

An excess of ethereal diazomethane was added to a solution of Nocathiacin I (100 mg) in 15 ml of tetrahydrofuran:chloroform:methanol (1:1:1). The solution was concentrated in vacuo and the residue chromatographed on silica (10 g) with chloroform:methanol:water (95:5:1) as eluent to afford 13 mg of the product with 73% purity together with a monomethylated thiazolyl peptide derivative: MS (MH+): 1465.

Method b:

To a solution of nocathiacin I (2.00 g, 1.39 mmol) in N,N-dimethylformamide (14 mL) were added cesium carbonate (1.81 g, 5.57 mmol) and tetra-n-butylammonium iodide (261 mg, 0.71 mmol), and the mixture was stirred at room temperature for 5 min. To this mixture was added dimethyl sulfate (1.32 mL, 13.9 mmol) and the mixture stirred at room temperature for 3 h. The resulting light yellow hazy solution was mixed with a minimum amount of N,N-dimethylformamide to a clear solution which was purified by preparative HPLC (C-18 reverse phase silica gel, MeOH/H2O/0.1% TFA system) to obtain 1.9 g of the title compound as the TFA salt: MS (MH+) 1465; HRMS (ES) calcd. for $C_{63}H_{65}N_{14}O_{18}S_5$ (MH+): 1465.320, Found: 1465.319.

EXAMPLE 19

Formula I: $R^1$=$R^2$=CH$_2$CO$_2$CH$_3$, Z=NHC(=CH$_2$)CONH$_2$

To a solution of nocathiacin I (1.00 g, 0.69 mmol) in anhydrous N,N-dimethylformamide (8 mL) was added cesium carbonate (0.50 g, 1.52 mmol), and the mixture was treated with methyl bromoacetate (0.15 mL, 1.52 mmol) and the mixture stirred at room temperature for 2 h. The mixture was diluted with a 20% methanol/chloroform solution, filtered the insoluble materials and purified by column chromatography (silica gel, 2–15% MeOH/CHCl$_3$) to obtain 416 mg of the title compound as tan color solid: MS (MH+) =1581, MS (M−H)=1579. This compound was also prepared from nocathiacin I and methyl bromoacetate (8 eq.) by the use of diisopropylethyamine (10 eq.) and a catalytic amount of BEMP as base in DMF.

EXAMPLE 20

Formula I: $R^1$=$R^2$=CH$_2$CO$_2$H, Z=NHC(=CH$_2$)CONH$_2$

To a suspension of the product of example 19 (0.1 g, 0.063 mmol) in dry benzene (2.0 mL) was added tri-n-butyl tin oxide (0.14 mL, 0.025 mmol). The mixture was heated to reflux and held there for 5 h. A reaction aliquot at this time indicates total consumption of starting material and 1 major product by HPLC. Reaction was cooled to room temperature and 1N hydrochloric acid (0.25 mL) was added while stirring. After five minutes of stirring, the solvents were removed under reduced pressure, producing a yellow solid.

The solid was dissolved in a 3:1 acetonitrile/water solution (2 mL) and filtered via syringe filter and purified by preparative HPLC (C-18 reverse phase silica gel, Methanol/Water/0.1%TFA as mobile phase) to obtain 6 mg of the title compound as a yellow solid (1 TFA salt): MS (MH+)=1554, MS (M−H)=1552.

EXAMPLE 21

Formula I: $R^1=R^2=P(O)(CH_3)OH$, $Z=NHC(=CH_2)CONH_2$

Nocathiacin 1 (2.0 g, 1.4 mmol) was suspended in dichloromethane (20 ml). Diisopropylethylamine (0.72 ml, 4.1 mmol) was added and the mixture was cooled to 0° C. Methylphosphonic dichloride (0.54 g, 4.1 mmol) was added and the mixture was stirred 30 min at 0° C. The mixture was quenched with saturated aqueous sodium bicarbonate (20 ml) and concentrated in vacuo. The residue was suspended in water (300 ml) and the remaining solids were filtered off. The aqueous filtrate was purified by chromatography (preparative C18, ODS-A, S-75 μm, 20% acetonitrile/water). Product containing fractions were concentrated under vacuum on a cold bath (8° C.) to yield the product as a white powder (0.4 g, 21% yield): Anal. Calcd. for $C_{63}H_{66}N_{14}O_{22}P_2S_5 \cdot 0.6Na \cdot 7.7H_2O$: C, 43.35; H, 4.67; N, 11.23; S, 9.18; Na, 0.79. Found: C, 43.07; H, 4.71; N, 11.00; S, 9.42; Na, 0.74; LRMS (ESI+): m/z=1593.6; (ESI−) m/z=1591.31.

EXAMPLE 22

Formula I: $R^1=R^2=CH_2OP(O)(OH)_2$, $Z=NHC(=CH_2)CONH_2$

A solution of nocathiacin I (5.00 g, 3.48 mmol) in N,N-dimethylformamide (150 mL) was treated with BTPP (2.28 g, 7.30 mmol) and stirred for approximately 10 minutes, during which a deeper red color developed. The reaction was treated with O-chloromethyl-O',O''-di-tert-butyl phosphate (1.89 g, 7.30 mmol) and stirred at room temperature for 2 hours. The solvent was removed by rotary evaporator. The residue was taken up in ca. 30–40% acetonitrile in water, along with a small volume of N,N-dimethylformamide to assist with solubilization, and loaded onto a C-18 reverse phase column and eluted with 10% acetonitrile in water, increasing to 35% acetonitrile in water by stepwise gradient, resulting in the separation of mono- and bis-adduct. Fractions were allowed to stand for 16 hours, during which time the product underwent a loss of tert-butyl group on each phosphate moiety, resulting in the bis(mono-tert-butyl) intermediate. Appropriate fractions were lyophilized to give the bis(mono-tert-butyl) adduct intermediate, which was then treated with trifluoroacetic acid (5 mL) in dichloromethane (5 mL). The reaction was stopped by removal of solvent by rotary evaporator after HPLC indicated no tert-butyl intermediate remained. The crude residue was treated with water and saturated sodium bicarbonate solution was added to bring about dissolution of solids. The solution was purified by C-18 MPLC, eluting with 10% acetonitrile in water, increasing to 22.5% acetonitrile in water. Appropriate fractions were combined and concentrated by rotary evaporator. The aqueous solution was lyophilized, resulting in the product (226 mg, bis-sodium salt) as a yellow lyophilized solid. MS (MH+)=1657.4, MS (M−H)=1655.10.

EXAMPLES 23 AND 24

Formula I: $R^1=H$, $R^2=COMe$, $Z=NHC(=CH_2)CONH_2$ and Formula I: $R^1=COMe$, $R^2=H$, $Z=NHC(=CH_2)CONH_2$ To a stirred suspension of nocathiacin I (2.88 g, 2.0 mmol) in ethyl acetate (50 mL) was added acetic anhydride (0.5 mL, 5.3 mmol) followed by sodium bicarbonate (1.51 g, 18.0 mmol) and stirred at 50° C. for 1 h. Then chloroethyl chloroformate (1.10 mL, 10.0 mmol) was slowly added and continued stirring at 50° C. for additional 1.5 h. The reaction mixture was cooled to room temperature and allowed to age overnight. The solvent was removed under reduced pressure, dissolved in water, and purified on an MPLC (C18 column) using acetonitrile-water (10–35%) containing 0.01% HCl as an eluent. The fractions containing the products were combined, concentrated, and freeze-dried to give 1.50 g and 0.75 g of the products (as HCl salts) as yellow powders. $^1$H NMR (DMSO, 500 MHz): δ 11.30 (1H, s), 10.05 (1H, s), 9.23 (1H, s), 8.80–8.64 (3H, br m), 8.58 (1H, s), 8.54 (1H, s), 8.22 (1H, s), 8.08 (1H, s), 8.03 (1H, s), 7.90–7.80 (1H, br m), 7.72–7.61 (2H, br m), 7.44 (1H, t, J=7.7 Hz), 7.28 (1H, d, J=7.2 Hz), 7.23 (1H, d, J=8.0 Hz), 6.36 (2H, br s), 6.07 (1H, d, J=12.3 Hz), 5.76 (2H, br s), 5.70 (1H, d, J=8.3 Hz), 5.15 (1H, br s), 5.09–5.04 (2H, m), 4.92 (1H, br s), 4.63 (1H, br s), 4.38 (1H, d, J=9,6 Hz), 4.32 (1H, br s), 4.13 (1H, d, J=10.3 Hz), 4.06 (1H, d, J=6.8 Hz), 3.93–3.89 (3H, m), 3.85 (1H, d, J=7 Hz), 3.57 (5H, br s), 3.09 (1H, s), 2.88–2.85 (5H, br m), 2.24 (1H, br s), 2.20–2.000 (6H, m), 1.92 (1H, d, J=14,5 Hz), 1.55 (3H, s), 1.15 (3H, s), 0.78 (3H, d, J=6.9 Hz). HRMS (ES) calcd. for $C_{63}H_{63}N_{14}O_{19}S_5$ (M+H): 1479.299, found: 1479.299. and $^1$H NMR (DMSO, 500 MHz): δ 9.93 (1H, s), 9.28 (1H, s), 8.78 (2H, br s), 8.67 (1H, br s), 8.64–8.54 (2H, m), 8.41 (1H, s), 8.23 (1H, s), 8.19 (1H, s), 8.13–8.08 (1H, m), 7.79–7.61 (3H, m), 7.44 (1H, t, J=7.6 Hz), 7.35 (1H, d, J=7.8 Hz), 7.28 (1H, d, J=7.1 Hz), 6.56 (1H, s), 6.38 (1H, s), 6.07 (1H, d, J=12.2 Hz), 5.80 (1H, s), 5.76–5.69 (2H, m), 5.10–5.04 (3H, m), 4.88 (1H, br s), 4.60 (1H, br m), 4.39 (1H, d, J=9.6 Hz), 4.31–4.29 (1H, m), 4.13 (1H, d, J=10.3 Hz), 4.06 (1H, d, J=9.4 Hz), 3.93 (3H, s), 3.90–85 (2H, m), 3.43 (4H, br m), 3.1 (1H, s), 2.92–2.80 (4H, m), 2.14–1.91 (7H, m), 1.55 (3H, s), 1.16 (3H, s), 0.78 (3H, d, J=6.8 Hz). HRMS (ES) calcd. for $C_{63}H_{63}N_{14}O_{19}S_5$ (M+H): 1479.299, found: 1479.298.

EXAMPLE 25

(Formula I: $R^1=-CO(CH_2)_2CO_2CH_2CH_3$, $R^2=H$, $Z=NHC(=CH_2)CONH_2$

Ethyl succinylchloride (0.14 mmol) was added to a mixture of nocathiacin I (0.035 mmol) in pyridine (0.5 ml) at 0° C. The mixture was stirred for approximately 10 min then chloroform (1 ml) was added, and the solvent was removed at reduced pressure. The residue was further evaporated to dryness, and the resulting light yellow solid was further purified by prep HPLC. The product containing fractions were frozen and lyophilized, resulting in 20 mg of the product as a yellow solid: MS (MH+)=1565.

EXAMPLES 26 AND 27

Formula I: $R^1=R^2=$2-(N-morpholinyl)ethyl, Z=NHC(=CH$_2$)CONH$_2$ and Formula I: $R^1=$H, $R^2=$2-(N-morpholinyl)ethyl, Z=NHC(=CH$_2$)CONH$_2$ To a vigorously stirred suspension of nocathiacin I (144 mg, 0.1 mmol) in water (5 mL) was added triethylamine (70 µL, 0.5 mmol) followed by 1-(2-chloroethyl) morpholine hydrochloride (37 mg, 0.2 mmol). The resulting clear reaction mixture was stirred at room temperature for 17 h, and then purified by using preparative HPLC with methanol/water (contains 0.1% TFA). The fractions containing products were combined, concentrated, and freeze dried to afford the desired products as their TFA salts, 17.4 mg of the disubstituted product and 90 mg of the mono substituted product:

Formula I: $R^1=R^2=$2-(N-morpholinyl)ethyl, Z=NHC(=CH$_2$)CONH$_2$: $^1$HNMR (500 MHz, DMSO-d6) δ: 10.10 (1H, s), 9.18 (1H, s), 8.67 (1H, s), 8.63–8.57 (2H, m), 8.55 (1H, s), 8.31 (1H, br s), 8.21 (1H, s), 8.19 (1H, s), 7.88 (1H, s), 7.80–7.75 (2H, m), 7.70–7.66 (1H, m), 7.48 (1H, t, J=7.5 Hz), 7.32 (1H, d, J=4.6 Hz), 7.17 (1H, d, J=8.5 Hz), 6.57 (1H, s), 6.38 (1H, br m), 6.03 (1H, d, J=12.5 Hz), 5.87 (1H, d, J=10.7 Hz), 5.81 (1H, s), 5.72 (1H, d, J=10.1 Hz), 5.36 (1H, d, J=7.3 Hz), 5.10 (1H, s), 5.08–5.04 (2H, m), 4.86 (1H, s), 4.85–4.80 (2H, m), 4.72 (1H, J=9.5 Hz), 4.38 (2H, d, J=9.8 Hz), 4.12 (2H, d, J=9.8 Hz), 4.01–3.85 (7H, m), 3.54–3.25 (19H, m), 3.10 (1H, s), 2.87 (6H, br s), 2.14–2.09) 1H, m), 2.02 (3H, s),1.94 (1H, d, J=14.0 Hz), 1.24 (2H, br s), 1.13 (3H, d, J=4.6 Hz), 0.79 (3H, d, J=6.7 Hz). HRMS calcd for C73H83N16O20S5 (M+H): 1663.457; found: 1663.462.

Formula I: $R^1=$H, $R^2=$2-(N-morpholinyl)ethyl: $^1$HNMR (500 MHz, DMSO-d6) δ: 11.41 (1H, s), 10.05 (1H, s), 9.23 (1H, s), 8.66–8.56 (4H, m), 8.55 (1H, s), 8.22 (1H, s), 8.13 (1H, s), 8.10 (1H, s), 7.86 (1H, s), 7.75 (1H, d, J=10.8 Hz), 7.72 (1H, d, J=7 Hz), 7.63 (1H, s), 7.50 (1H, t, J=7.8 Hz), 7.33 (1H, d, J=7.1 Hz), 7.14 (1H, d, J=8.3 Hz), 6.38 (1H, d, J=13.3 Hz), 6.37 (1H, s), 6.02 (1H, d, J=12.4 Hz), 5.88 (1H, d, J=12.6 Hz), 5.76 (1H, s), 5.71 (1H, d, J=9.7 Hz), 5.38 (1H, d, J=8.5 Hz), 5.24 (1H, br s), 5.10 (1H, s), 5.06 (1H, d, J=4.7 Hz), 4.85 (1H, d, J=10.3 Hz), 4.75 (1H, d, J=11.2 Hz), 4.39 (1H, d, J=9.4 Hz), 4.25 (1H, br s), 4.12 (2H, t, J=11.3 Hz), 3.92 (3H, s), 3.87 (1H, d, J=7.2 Hz), 3.51–3.42 (13H, m), 3.41 (1H, d, J=5.2 Hz), 3.10 (1H, s), 2.87 (6H, s), 2.54 (1H, s), 2.43 (1H, br s), 2.12 (1H, d, J=9.8 Hz), 2.02 (3H, s), 1.93 (1H, d, J=14.6 Hz), 1.58 (3H, s), 1.15 (3H, d, J=5.0 Hz), 0.78 (3H, d, J=6.8 Hz). HRMS calcd for C67H72N15O19S5 (M+H): 1550.373; found: 1550.370.

In a similar fashion compounds in Examples 28–87 described in Table 1 were prepared using the general reactions or common variations of the reactions shown above. Any further modifications are well known to those skilled in the art.

TABLE 1

Analytical data for examples 28–87.

| Number | R$^1$ | R$^2$ | Z NHC(=CH$_2$)CONH$_2$ unless noted | M + 1 LRMS/HRMS | M − 1 LRMS/HRMS |
|---|---|---|---|---|---|
| 28 | —(CH$_2$)$_3$SO$_3$Na | H | | 1559 | 1557 |
| 29 | COtBu | H | | 1521.58 | 1519.37 |
| 30 | COCH$_2$CH$_2$CO$_2$allyl | H | | 1577.25 | 1575.89 |
| 31 | COC(Me)$_2$CO$_2$CH$_2$Ph | H | | 1641.50 | 1639.70 |
| 32 | —COPh—pBr | H | | 1621.54 | |
| 33 | P(O)(H)ONa | H | | 1502 | |
| 34 | —P(O)(OCH$_2$Ph)$_2$ | H | | 1698 | |
| 35 | —P(O)(OH)OCH$_2$CH$_2$Cl | H | | 1579.49 | 1577.10 |
| 36 | H | —CH$_2$CH$_2$OH | | 1481.3 | 1479.6 |
| 37 | H | —CH$_2$CO$_2$Me | | 1509.2 | |
| 38 | H | (sugar structure) | | 1679.3 | |
| 39 | H | —COCH=CO$_2$H | | 1535.2 | |
| 40 | H | —CH$_2$OP(O)(OtBu)$_2$ | | 1660.9 | 1657.8 |
| 41 | H | —CH$_2$OP(O)(OEt)$_2$ | | 1587.3 | 1585.5 |
| 42 | H | —CH$_2$CH$_2$CH$_2$NH$_2$ | | 1494 | 1492 |
| 43 | H | —CH$_2$CH$_2$CH$_2$N$_3$ | | 1501 | |
| 44 | H | —CH$_2$CH$_2$CO$_2$Na | | 1507 | 1509 |
| 45 | H | —CH$_2$OCH$_2$CH$_2$SiMe$_3$ | | 1566.9 | |
| 46 | H | (propyl-imidazole structure) | | 1531 | |

TABLE 1-continued

Analytical data for examples 28–87.

| Number | R¹ | R² | Z NHC(=CH$_2$)CONH$_2$ unless noted | M + 1 LRMS/HRMS | M − 1 LRMS/HRMS |
|---|---|---|---|---|---|
| 47 | H | 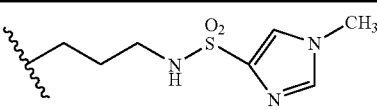 | | 1638 | |
| 48 | H | 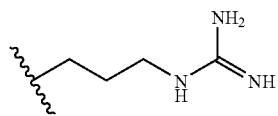 | | 1537 | 1535 |
| 49 | H | 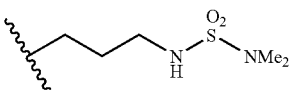 | | | 1599 |
| 50 | H | 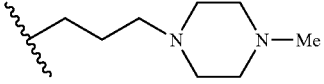 | | 1578 | |
| 51 | H | —CH$_2$CH$_2$CH$_2$NEt$_2$ | | 1551 | |
| 52 | H | 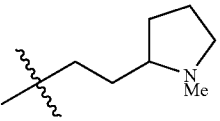 | | 1548 | |
| 53 | H | —(CH$_2$)$_3$SO$_3$H | NH$_2$ | 1490.3 | 1488 |
| 54 | H | —CH$_2$OP(O)(OH)(OtBu) | | 1603.7 | 1601.3 |
| 55 | H | —CH$_2$(CH$_2$CH$_2$O)$_4$CH$_3$ | | 1626 | |
| 56 | H | —CH$_2$(CH$_2$CH$_2$O)$_6$H | | 1701 | |
| 57 | H | 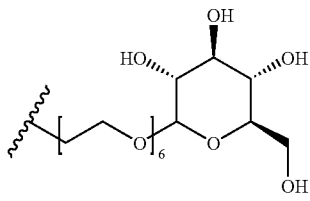 | | 1863.3 | 1861.1 |
| 58 | H | 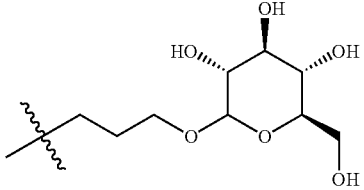 | | 1657.0 | 1655.3 |
| 59 | H | —(CH$_2$)$_4$SO$_3$H | NH$_2$ | 1505.7 | 1503.6 |
| 60 | H | —CONHMe | | 1494.3 | 1492.3 |
| 61 | H | —CONMeCH$_2$CH$_2$OH | | 1538.9 | |
| 62 | H | —CONH(CH$_2$CH$_2$O)$_4$CH$_3$ | | 1670 | |
| 63 | H | —CONH(CH$_2$CH$_2$O)$_4$H | | 1744 | |
| 64 | H | —SO$_3$Na | | 1519 | 1517 |
| 65 | H | —P(O)(OCH$_2$CH$_2$Cl)(OH) | | 1579.5 | 1577.2 |
| 66 | —CH$_2$Ph | —CH$_2$Ph | | 1618.5 | 1616.6 |
| 67 | —(CH$_2$)$_3$SO$_3$Na | —(CH$_2$)$_3$SO$_3$Na | | 1681.8 | 1679.9 |
| 68 | —CH$_2$CO$_2$tBu | —CH$_2$CO$_2$tBu | | 1665.6 | 1664.12 |
| 69 | —CH$_2$CONHCH$_2$CH$_2$NHBOC | —CH$_2$CONHCH$_2$CH$_2$NHBOC | | 1838.8 | 1835.68 |
| 70 | —CH$_2$CONHCH$_2$CN | —CH$_2$CONHCH$_2$CN | | 1629.4 | 1627.8 |
| 71 | —CH$_2$CONMe$_2$ | —CH$_2$CONMe$_2$ | | 1607.4 | 1605.7 |
| 72 | —CH$_2$CO$_2$CH$_2$CH$_2$OH | —CH$_2$CO$_2$CH$_2$CH$_2$OH | | 1641.3 | |
| 73 | —CH$_2$OP(O)(OtBu)$_2$ | —CH$_2$OP(O)(OtBu)$_2$ | | 1882.1 | 1879.8 |
| 74 | —CH$_2$CH=CH$_2$ | —CH$_2$CH=CH$_2$ | | 1517 | |

TABLE 1-continued

Analytical data for examples 28–87.

| Number | R¹ | R² | Z NHC(=CH$_2$)CONH$_2$ unless noted | M + 1 LRMS/HRMS | M − 1 LRMS/HRMS |
|---|---|---|---|---|---|
| 75 | —CH$_2$C≡CH | —CH$_2$C≡CH | | 1513 | |
| 76 | —CH$_2$CN | —CH$_2$CN | | 1515.6 | 1514.27 |
| 77 | —CH$_2$CH$_2$OH | —CH$_2$CH$_2$OH | | 1525.3 | 1523.6 |
| 78 | —CH$_2$CONH$_2$ | —CH$_2$O(CH$_2$)$_2$SiMe$_3$ | | 1624 | 1622 |
| 79 | —CH$_2$Ph | —CH$_2$O(CH$_2$)$_2$SiMe$_3$ | | 1657 | |
| 80 | —CH$_2$(CH$_2$CH$_2$O)$_4$CH$_3$ | —CH$_2$(CH$_2$CH$_2$O)$_4$CH$_3$ | | | 1815 |
| 81 | —CH$_2$OP(O)(OtBu)(ONa) | —CH$_2$OP(O)(OtBu)(ONa) | | 1768 | |
| 82 | —CH$_2$CO$_2$tBu | —CH$_2$CO$_2$tBu | NH$_2$ | | 1594.1 |
| 83 | Me | Me | NH$_2$ | 1396.1 | 1394.1 |
| 84 | —CH$_2$O(CH$_2$)$_2$SiMe$_3$ | —CH$_2$O(CH$_2$)$_2$SiMe$_3$ | | 1697 | |
| 85 | —COPh—pBr | —COPh—pBr | | 1805.7 | |
| 86 | —P(O)(OH)OCH$_2$CH$_2$Cl | —P(O)(OH)OCH$_2$CH$_2$Cl | | 1723.9 | 1720.9 |
| 87 | 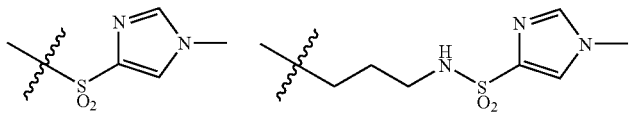 | | | 1783 | 1781 |

Antibiotic Activity of the Compounds

To demonstrate its antimicrobial properties, the minimum inhibitory concentration (MIC) for compounds of the invention was obtained against a variety of bacteria using a conventional broth micro dilution assay in accordance with standards recommended by the National Committee for Clinical Laboratory Standards (NCCLS). The serial broth dilution method used Mueller-Hinton medium except for the *Streptococcus pneumoniae* which was tested in 50% Mueller-Hinton medium and 50% Todd Hewitt medium. The final bacterial inoculate contained approximately 5×10$^5$ cfu/well and was run on microtiter plates. The volume of each well was 100 μL and the plates were incubated at 35° C. for 18 hours in ambient air. The MIC was defined as the lowest drug concentration that prevented visible growth. Some of the results obtained are shown in Table 2 below and demonstrate that compounds of this invention have utility in treating bacterial infections.

TABLE 2

Antibacterial activity of Formula I compounds.

| Example | MIC (μg/mL) Staphylococcus aureus A15090 | MIC (μg/mL) Streptococcus pneumoniae A28272 | MIC (μg/mL) Enterococcus faecalis A20688 |
|---|---|---|---|
| 1 | 0.015 | 0.003 | 0.015 |
| 2 | 1.0 | 0.015 | 0.125 |
| 3 | 1.0 | 0.25 | 2.0 |
| 4 | 0.06 | 0.06 | 0.25 |
| 5 | 0.125 | 0.06 | 0.25 |
| 6 | 0.03 | 0.003 | 0.125 |
| 7 | 0.125 | 0.007 | 0.125 |
| 8 | 0.5 | 0.03 | 0.25 |
| 9 | 2.0 | 0.125 | 4.0 |
| 10 | 0.5 | 0.015 | 0.5 |
| 11 | 16 | 0.06 | >128 |
| 12 | 0.25 | 0.015 | 1.0 |
| 13 | 0.015 | 0.003 | 0.03 |
| 14 | >128 | 0.5 | 2.0 |
| 15 | ≦0.001 | 0.007 | 0.03 |
| 16 | 0.003 | 0.0005 | 0.003 |
| 17 | 0.25 | 0.06 | 1.0 |
| 18 | 0.007 | 0.001 | 0.015 |
| 19 | 0.06 | 0.003 | 0.125 |
| 20 | 16 | 0.5 | >128 |
| 21 | 1.0 | 0.50 | 1.0 |
| 22 | 0.125 | 0.015 | 0.25 |
| 23 | 0.03 | 0.06 | 0.25 |
| 24 | 0.03 | 0.03 | 0.015 |
| 26 | 1.0 | 0.03 | 0.25 |
| 27 | 0.25 | 0.015 | 0.06 |
| 28 | 2.0 | 0.25 | 32 |
| 31 | 0.25 | 0.06 | 0.5 |
| 32 | 1.0 | 0.015 | 1.0 |
| 34 | 0.25 | 0.125 | 1.0 |
| 35 | 1.0 | 0.03 | 1.0 |
| 36 | 0.25 | 0.007 | 0.25 |
| 37 | 0.03 | 0.001 | 0.06 |
| 38 | 0.125 | 0.001 | 0.03 |
| 40 | 0.125 | 0.015 | 0.25 |
| 41 | 0.015 | 0.001 | 0.03 |
| 42 | 0.25 | 0.06 | 1.0 |
| 43 | 0.125 | 0.03 | 0.06 |
| 44 | 0.125 | 0.03 | 0.25 |
| 45 | 2.0 | 0.03 | 1.0 |
| 46 | 0.5 | 0.015 | 1.0 |
| 47 | 0.06 | 0.015 | 0.25 |
| 48 | 1.0 | 0.03 | 2 |
| 49 | 0.5 | 0.007 | 0.25 |
| 50 | 1.0 | 0.03 | 1.0 |
| 51 | 0.5 | 0.015 | 0.125 |
| 52 | 0.5 | 0.06 | 0.25 |
| 53 | 0.25 | 0.125 | 1.0 |
| 55 | 8.0 | 1 | 8.0 |
| 56 | 0.125 | 0.007 | 0.5 |
| 57 | 4.0 | 0.06 | >128 |
| 58 | 16 | 0.06 | >128 |
| 59 | 16 | 0.5 | >128 |
| 60 | 0.125 | 0.001 | 0.06 |
| 61 | 0.03 | 0.0005 | 0.03 |
| 62 | 0.125 | 0.015 | 0.125 |
| 63 | 0.06 | 0.003 | 0.06 |
| 64 | 1.0 | 0.06 | 0.125 |

TABLE 2-continued

Antibacterial activity of Formula I compounds.

| Example | MIC (μg/mL) Staphylococcus aureus A15090 | MIC (μg/mL) Streptococcus pneumoniae A28272 | MIC (μg/mL) Enterococcus faecalis A20688 |
| --- | --- | --- | --- |
| 65 | 0.25 | 0.03 | 0.5 |
| 66 | 2.0 | 0.001 | 0.25 |
| 67 | >128 | 0.5 | 128 |
| 68 | 8.0 | 0.007 | 4.0 |
| 69 | 16 | 0.25 | 64 |
| 70 | 4.0 | 0.06 | 0.5 |
| 71 | 8.0 | 0.125 | 4.0 |
| 72 | 4.0 | 0.06 | 4.0 |
| 73 | 2.0 | 0.25 | 2.0 |
| 74 | 0.06 | 0.0005 | 0.25 |
| 75 | 0.03 | 0.0005 | 0.06 |
| 77 | 0.5 | 0.03 | 1.0 |
| 78 | 64 | 0.06 | 16 |
| 79 | 1.0 | 0.015 | 1.0 |
| 81 | 128 | 8 | >128 |
| 82 | 0.03 | 0.015 | 0.06 |
| 83 | 0.03 | 0.03 | 0.06 |
| 85 | 0.5 | 0.007 | 0.5 |
| 86 | 4.0 | 0.5 | 4.0 |
| 87 | 1.0 | 0.06 | 2.0 |

Many of the compounds of Formula I were evaluated for antibiotic activity in vivo in a systemic infection model using female ICR mice. The animals were infected intraperitonially (IP) with 6.5×10⁶ CFU of an overnight culture of *Staphylococcus aureus* A15090 suspended in 7% mucin. The compounds were tested at 4 dose levels, (25, 6.25, 1.56, and 0.39 mg/kg) and were prepared in a test formulation consisting of 10% DMSO, 5% Tween 80 and 85% water. A $PD_{50}$ (the dose of drug given which protects 50% of mice from mortality) experiment was run for 5 days. During this time, mortality of mice was checked every day and deaths were recorded. The cumulative mortality at each dose level was used to calculate a $PD_{50}$ value for each compound. Surviving mice were sacrificed at the end of day 5 by $CO_2$ inhalation. Actual calculation of the $PD_{50}$ was performed with a computer program using the Spearman-Karber procedure. The solution was administered subcutaneously (SC) at 1 and 4 hours post-infection. The in vivo efficacy, expressed as a $PD_{50}$ value, were found to be within the range of 0.16 to 10.00 mg/kg for several of the compounds, namely, Examples 5, 6, 7, 8, 12, 13, 17, 18, 21, 27, 37, 41, 47, 50, 53 and 63.

What is claimed is:

1. A compound of Formula I, including pharmaceutically acceptable salts thereof,

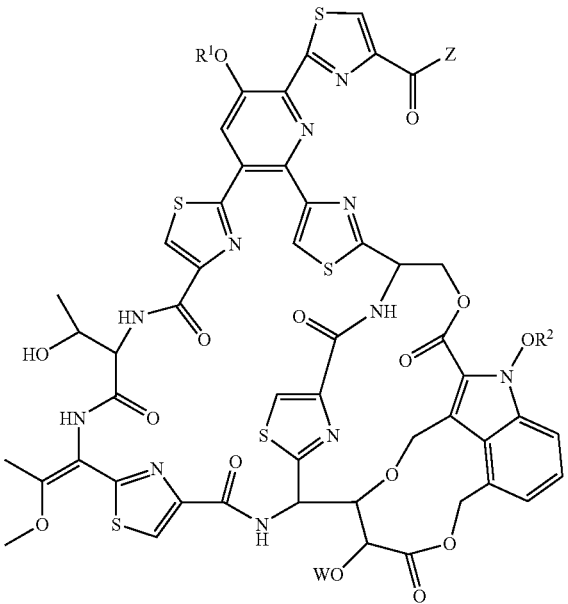

wherein:

W is

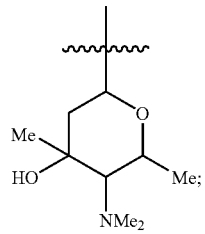

Z is selected from the group consisting of —NH₂ and

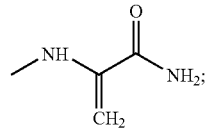

R¹ is selected from the group consisting of

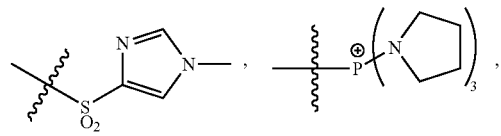

hydrogen, —P(O)A¹A², —C(O)C₁₋₆alkyl, —C(O)aryl, —C(O)NHC₁₋₆alkyl, —C(O)NHaryl, —(CH₂CH₂O)ₘMe, —C₁₋₆alkenyl, —C₁₋₆alkynyl, and —C₁₋₆alkyl; wherein said C₁₋₆alkyl is optionally substituted by one to six hydroxy or optionally substituted by one to two same or different substituents selected from the group consisting of (a)–(i):
(a) $CO_2R^3$;
(b) $CONR^4R^5$;
(c) $OP(O)A^1A^2$;
(d) $SO_3H$;
(e) $-O(CH_2)_nSiR^6{}_3$;
(f) heteroalicyclic selected from the group consisting of pyrrolidinyl, piperidinyl, piperazinyl, and morpholinyl;
(g) cyano;
(h) epoxy; and
(i) aryl;
and provided that $R^1$ and $R^2$ are not simultaneously H; $R^2$ is selected from the group consisting of

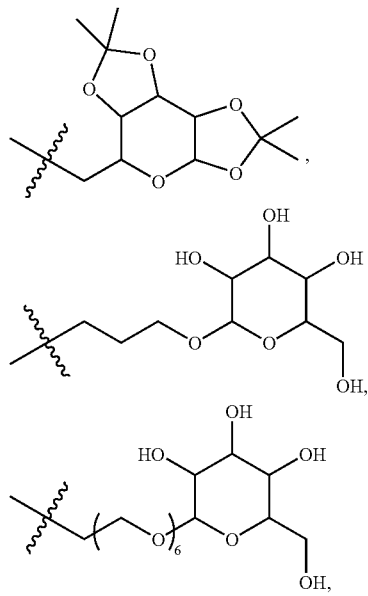

hydrogen, $-P(O)A^1A^2$, $-SO_3H$, $-C(O)C_{1-6}$alkyl, $-C(O)CH=CHCO_2R^3$, $-C(O)$aryl, $-C(O)N(H)(C_{1-6}$ alkyl-T), $-C(O)N(Me)(C_{1-6}$alkyl-T), $-(CH_2CH_2O)_p H$, $-(CH_2CH_2O)_q Me$, $-C_{1-6}$alkenyl, $-C_{1-6}$alkyl and $-C_{1-6}$alkynyl; wherein said $-C_{1-6}$ alkyl is optionally substituted by one to six hydroxy or optionally substituted by one to two same or different substituents selected from the group consisting of (j)–(v):
(j) halo;
(k) $CO_2R^3$;
(l) $CONR^4R^5$;
(m) $OP(O)A^1A^2$;
(n) $P(O)A^1A^2$;
(o) $SO_3H$;
(p) $-O(CH_2)_rSiR^6{}_3$;
(q) heterocyclic or heteroalicyclic selected from the group consisting of pyrrolidinyl, piperidinyl, piperazinyl, morpholinyl, imidazolyl, and pyridyl;
(r) cyano;
(s) azido;
(t) aryl;
(u) $NR^4R^5$; and
(v)

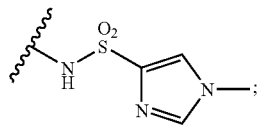

$R^3$ is selected from the group consisting of hydrogen, $C_{1-6}$alkyl, allyl, benzyl, 2-hydroxyethyl, and 2-tetrahydropyranyl;

$R^4$ and $R^5$ are each independently selected from the group consisting of hydrogen, $C_{1-6}$alkyl, $CH_2CN$, $CH_2CH_2NH$(t-butyloxycarbonyl), $C(=NH)NH_2$ and $SO_2N(C_{1-6}$alkyl$)_2$; or $R^4$ and $R^5$ taken together with the nitrogen to which they are attached form a heterocyclic or heteroalicyclic selected from the group consisting of pyrrolidinyl, piperidinyl, piperazinyl, morpholinyl, imidazolyl, and pyridyl;

$R^6$ is selected from $C_{1-6}$alkyl and phenyl;

$A^1$ and $A^2$ are each independently selected from the group consisting of hydrogen, $-C_{1-6}$alkyl, $-OC_{1-6}$alkyl, benzyloxy, 2-chloroethoxy, and hydroxy;

T is selected from the group consisting of hydrogen, $-OH$, $-(CH_2CH_2O)_sH$, $-(CH_2CH_2O)_tCH_3$ and $-NR^4R^5$;

m, n, p, q, r, s and t are independently 1–6; and aryl consists of a phenyl group optionally substituted with halo or $-CO_2R^3$.

2. A compound of claim 1, including pharmaceutically acceptable salts thereof, wherein Z is

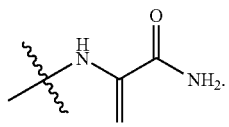

3. A compound of claim 1, including pharmaceutically acceptable salts thereof, wherein Z is $-NH_2$.

4. A compound of claim 2 selected from groups (a)–(q) consisting of:
(a) $R^1$ and $R^2$ are $CH_3$;
(b) $R^1$ and $R^2$ are $P(O)(CH_3)OH$;
(c) $R^1$ and $R^2$ are $CH_2OP(O)(OH)_2$;
(d) $R^1$ is $P(O)(CH_3)OH$ and $R^2$ is H;
(e) $R^1$ is

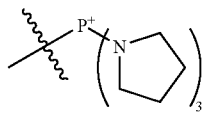

and $R^2$ is H;
(f) $R^1$ is H and $R^2$ is $P(O)(CH_3)OH$;
(g) $R^1$ is H and $R^2$ is $CH_2CONH_2$;
(h) $R^1$ is H and $R^2$ is $CH_2CO_2CH_3$;
(i) $R^1$ is H and $R^2$ is $CH_2CH_2CH_2SO_3H$;
(j) $R^1$ is H and $R^2$ is $CH_2P(O)(OEt)_2$;

(k) $R^1$ is H and $R^2$ is $CH_2OP(O)(OH)_2$;
(l) $R^1$ is H and $R^2$ is $CH_2CH_2Cl$;
(m) $R^1$ is H and $R^2$ is

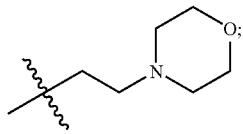

(n) $R^1$ is H and $R^2$ is $CH_3$;
(o) $R^1$ is H and $R^2$ is $CONH(CH_2CH_2O)_4H$;
(p) $R^1$ is H and R is

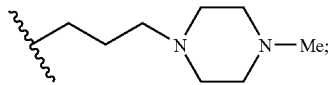

and (q) $R^1$ is H and $R^2$ is

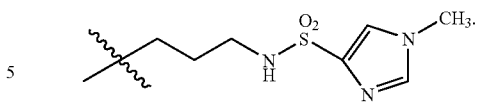

5. A compound of claim 3 where $R^1$ is H and $R^2$ is $CH_2CH_2CH_2SO_3H$.

6. A pharmaceutical composition which comprises a therapeutically effective amount of a compound of claim 1, and a pharmaceutically acceptable carrier, adjuvant, or diluent.

7. A method of treating or preventing bacterial or mycobacterial infection comprising administering to a mammal in need thereof a therapeutically effective amount of a compound of claim 1.

8. The method of claim 7, wherein said bacterial or mycobacterial infection is caused by a Gram-positive bacteria or a mycobacterium.

9. The method of claim 8, wherein said Gram-positive bacterial infection or mycobacterial infection is caused by a member selected from the group consisting of methicillin-resistant *Staphylococcus aureus*, vancomycin-resistant *Staphylococcus aureus*, vancomycin-resistant *Enterococcus faecalis*, vancomycin-resistant *Enterococcus faecium*, penicillin-resistant *Streptococcus pneumoniae* and *Mycobacteria tuberculosis*.

* * * * *